US012649704B2

(12) United States Patent
Maduskar et al.

(10) Patent No.: US 12,649,704 B2
(45) Date of Patent: Jun. 9, 2026

(54) PROCESSES FOR DEHYDROGENATING ALKANES AND ALKYL AROMATIC HYDROCARBONS

(71) Applicant: ExxonMobil Chemical Patents Inc., Baytown, TX (US)

(72) Inventors: Saurabh S. Maduskar, Houston, TX (US); Xiaoying Bao, Houston, TX (US); Keith H. Kuechler, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 170 days.

(21) Appl. No.: 18/579,707

(22) PCT Filed: Jul. 22, 2022

(86) PCT No.: PCT/US2022/038036
§ 371 (c)(1),
(2) Date: Jan. 16, 2024

(87) PCT Pub. No.: WO2023/018536
PCT Pub. Date: Feb. 16, 2023

(65) Prior Publication Data
US 2024/0327316 A1    Oct. 3, 2024

Related U.S. Application Data

(60) Provisional application No. 63/328,971, filed on Apr. 8, 2022, provisional application No. 63/232,959, filed on Aug. 13, 2021.

(51) Int. Cl.
| | |
|---|---|
| *C07C 5/41* | (2006.01) |
| *B01J 38/02* | (2006.01) |
| *B01J 38/12* | (2006.01) |

(52) U.S. Cl.
CPC ............... *C07C 5/417* (2013.01); *B01J 38/02* (2013.01); *B01J 38/12* (2013.01); *C07C 2523/42* (2013.01)

(58) Field of Classification Search
CPC ... C07C 5/417; C07C 2523/42; C07C 5/3337; C07C 2521/04; C07C 2521/10;
(Continued)

(56) References Cited

U.S. PATENT DOCUMENTS

| | | |
|---|---|---|
| 2,889,383 A | 6/1959 | Donald |
| 7,473,668 B2 | 1/2009 | Bartolini et al. |

(Continued)

FOREIGN PATENT DOCUMENTS

| | | |
|---|---|---|
| GB | 1107432 | 8/1965 |
| KR | 10-0699110 B1 | 3/2007 |

(Continued)

OTHER PUBLICATIONS

Ray Cocco and Jia Wei Chew, "50 years of Geldart classification," Powder Technology, vol. 428, Article No. 118861, Available online Aug. 2, 2023, <https://doi.org/10.1016/j.powtec.2023.118861!> (12 pages).

*Primary Examiner* — Ellen M McAvoy
(74) *Attorney, Agent, or Firm* — WOMBLE BOND DICKINSON (US) LLP; Kevin Davis

(57) ABSTRACT

A hydrocarbon feed can be contacted with dehydrogenation catalyst particles to produce a conversion effluent that includes coked catalyst particles and dehydrogenated hydrocarbon(s). The coked catalyst particles can be contacted with an oxidant and a fuel to produce a combustion effluent that can include catalyst particles lean in coke and a combustion gas. The catalyst particles lean in coke can be contacted with an oxidative gas at an oxidizing temperature for a duration of at least 30 seconds to produce conditioned catalyst (Continued)

particles that can have an activity that can be less than the coked catalyst particles. The conditioned catalyst particles can be contacted with a reducing gas to produce regenerated catalyst particles that can have a dehydrogenation activity that can be greater than the coked catalyst particles. The dehydrogenated hydrocarbon(s) can be cooled, compressed, and a plurality of products can be separated from the compressed gaseous stream.

25 Claims, 3 Drawing Sheets

(58) Field of Classification Search
CPC ............ C07C 2523/14; C07C 2523/58; C07C 2523/62; B01J 38/02; B01J 38/12; B01J 35/615; B01J 21/04; B01J 21/10; B01J 23/002; B01J 23/626; B01J 23/96; B01J 37/0201; B01J 38/06; B01J 38/10; B01J 38/16

See application file for complete search history.

(56) References Cited

U.S. PATENT DOCUMENTS

| | | | | |
|---|---|---|---|---|
| 9,091,433 | B2 | 7/2015 | Mabande et al. | |
| 9,511,356 | B2 | 12/2016 | Vaidya et al. | |
| 11,643,377 | B2 | 5/2023 | Pretz et al. | |
| 11,680,029 | B2 * | 6/2023 | Bao | B01J 38/10 |
| | | | | 585/660 |
| 11,760,702 | B2 * | 9/2023 | Bao | B01J 35/31 |
| | | | | 585/634 |
| 11,760,703 | B2 * | 9/2023 | Bao | C07C 5/417 |
| | | | | 585/634 |
| 11,859,136 | B2 * | 1/2024 | Bao | B01J 21/10 |
| 2004/0186333 | A1 | 9/2004 | Lattner | |
| 2010/0152021 | A1 | 6/2010 | Lew | |
| 2010/0298117 | A1 | 11/2010 | Levin et al. | |
| 2012/0123177 | A1 | 5/2012 | Pretz et al. | |
| 2018/0318812 | A1 | 11/2018 | Bedard et al. | |

FOREIGN PATENT DOCUMENTS

| | | |
|---|---|---|
| WO | 00/72967 A1 | 12/2000 |
| WO | 2000/72967 A1 | 12/2000 |
| WO | 2013/190574 A1 | 12/2013 |
| WO | 2020/009860 A1 | 1/2020 |

* cited by examiner

Time (hour)

PROCESSES FOR DEHYDROGENATING ALKANES AND ALKYL AROMATIC HYDROCARBONS

CROSS-REFERENCE TO RELATED APPLICATIONS

This application is a US national phase application of PCT Application Serial No. PCT/US2022/038036 having a filing date of Jul. 22, 2022, which claims priority to and the benefit of U.S. Provisional Application No. 63/232,959 having a filing date of Aug. 13, 2021, and U.S. Provisional Application No. 63/328,971 having a filing date of Apr. 8, 2022, the disclosures of all of which are incorporated herein by reference in their entireties.

FIELD

This disclosure relates to processes for dehydrogenating one or more alkanes and/or alkyl aromatic hydrocarbons. More particularly, this disclosure relates to processes for dehydrogenating one or more alkanes and/or one or more alkyl aromatic hydrocarbons in the presence of fluidized catalyst particles to produce an effluent that includes one or more olefins.

BACKGROUND

Catalytic dehydrogenation of alkanes and/or alkyl aromatic hydrocarbons are industrially important chemical conversion processes that are endothermic and equilibrium-limited. The dehydrogenation of alkanes, e.g., $C_2$-$C_{16}$ alkanes, and/or alkyl aromatic hydrocarbons, e.g., ethylbenzene, can be done through a variety of different supported catalyst particle systems such as the Pt-based, Cr-based, Ga-based, V-based, Zr-based, In-based, W-based, Mo-based, Zn-based, and Fe-based systems. Among the existing propane dehydrogenation processes, a certain process uses an alumina supported chromia catalyst that provides one of the highest propylene yields at approximately 50% (55% propane conversion at 90% propylene selectivity), which is obtained at a temperature of approximately 560° C. to 650° C. and at a low pressure of 20 kPa-absolute to 50 kPa-absolute. It is desirable to increase the propylene yield without having to operate at such low pressure to increase the efficiency of the dehydrogenation process.

Increasing the temperature of the dehydrogenation process is one way to increase the conversion of the process according to the thermodynamics of the process. For example, at 670° C., 100 kPa-absolute, in the absence of any inert/diluent, the equilibrium propylene yield has been estimated via simulation to be approximately 74%. At such high temperature, however, the catalyst particles deactivate very rapidly and/or the propylene selectivity becomes uneconomically low. The rapid deactivation of the catalyst particles is believed to be caused by coke depositing onto the catalyst particles and/or agglomeration of the active phase. Coke can be removed by combustion using an oxygen-containing gas, however, agglomeration of the active phase is believed to be exacerbated during the combustion process, which rapidly reduces the activity and stability of the catalyst particles.

There is a need, therefore, for improved processes for dehydrogenating alkanes and/or alkyl aromatic hydrocarbons. This disclosure satisfies this and other needs.

SUMMARY

Processes for upgrading alkanes and/or alkyl aromatic hydrocarbons are provided. In some embodiments, the process for upgrading a hydrocarbon can include (I) contacting a hydrocarbon-containing feed with fluidized dehydrogenation catalyst particles in a conversion zone to effect dehydrogenation of at least a portion of the hydrocarbon-containing feed to produce a conversion effluent that can include coked catalyst particles and one or more dehydrogenated hydrocarbons. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof. The hydrocarbon-containing feed can contact the catalyst particles at a weight hourly space velocity in a range from 0.1 $hr^{-1}$ to 1,000 $hr^{-1}$, based on the weight of any $C_2$-$C_{16}$ alkanes and any $C_8$-$C_{16}$ aromatic hydrocarbons in the hydrocarbon-containing feed. A weight ratio of the fluidized dehydrogenation catalyst particles to a combined amount of any $C_2$-$C_{16}$ alkanes and any $C_8$-$C_{16}$ aromatic hydrocarbons can be in a range from 3 to 100. The hydrocarbon-containing feed and the catalyst particles can be contacted at a temperature in a range from 600° C. to 750° C. The process can also include (II) separating from the conversion effluent a first particle stream rich in the coked catalyst particles and a first gaseous stream rich in the one or more dehydrogenated hydrocarbons. The process can also include (III) contacting at least a portion of the coked catalyst particles in the first particle stream with an oxidant and a fuel in a combustion zone to effect combustion of at least a portion of the coke to produce a combustion effluent that can include catalyst particles lean in coke and a combustion gas. A dehydrogenation activity of the catalyst particles lean in coke can be less than a dehydrogenation activity of the coked catalyst particles. The process can also include (IV) separating a second particle stream rich in the catalyst particles lean in coke and a second gaseous stream rich in the combustion gas from the combustion effluent. The process can also include (V) contacting at least a portion of the catalyst particles lean in coke in the second particle stream with an oxidative gas in an oxygen soak zone at an oxidizing temperature in a range from 620° C. to 1,000° C. for a duration of at least 30 seconds to produce conditioned catalyst particles having an activity that can be less than the coked catalyst particles. The process can also include (VI) contacting at least a portion of the conditioned catalyst particles with a reducing gas in a reduction zone to produce regenerated catalyst particles having a dehydrogenation activity that can be greater than the coked catalyst particles. The process can also include (VII) contacting an additional quantity of the hydrocarbon-containing feed with at least a portion of the regenerated catalyst particles in the conversion zone to produce an additional quantity of the conversion effluent that can include re-coked catalyst particles and an additional quantity of the one or more dehydrogenated hydrocarbons. The process can also include (VIII) cooling the first gaseous stream to produce a cooled gaseous stream. The process can also include (IX) compressing at least a portion of the cooled gaseous stream to produce a compressed gaseous stream. The process can also include (X) separating a plurality of products from the compressed gaseous stream.

DETAILED DESCRIPTION

Figure 1:
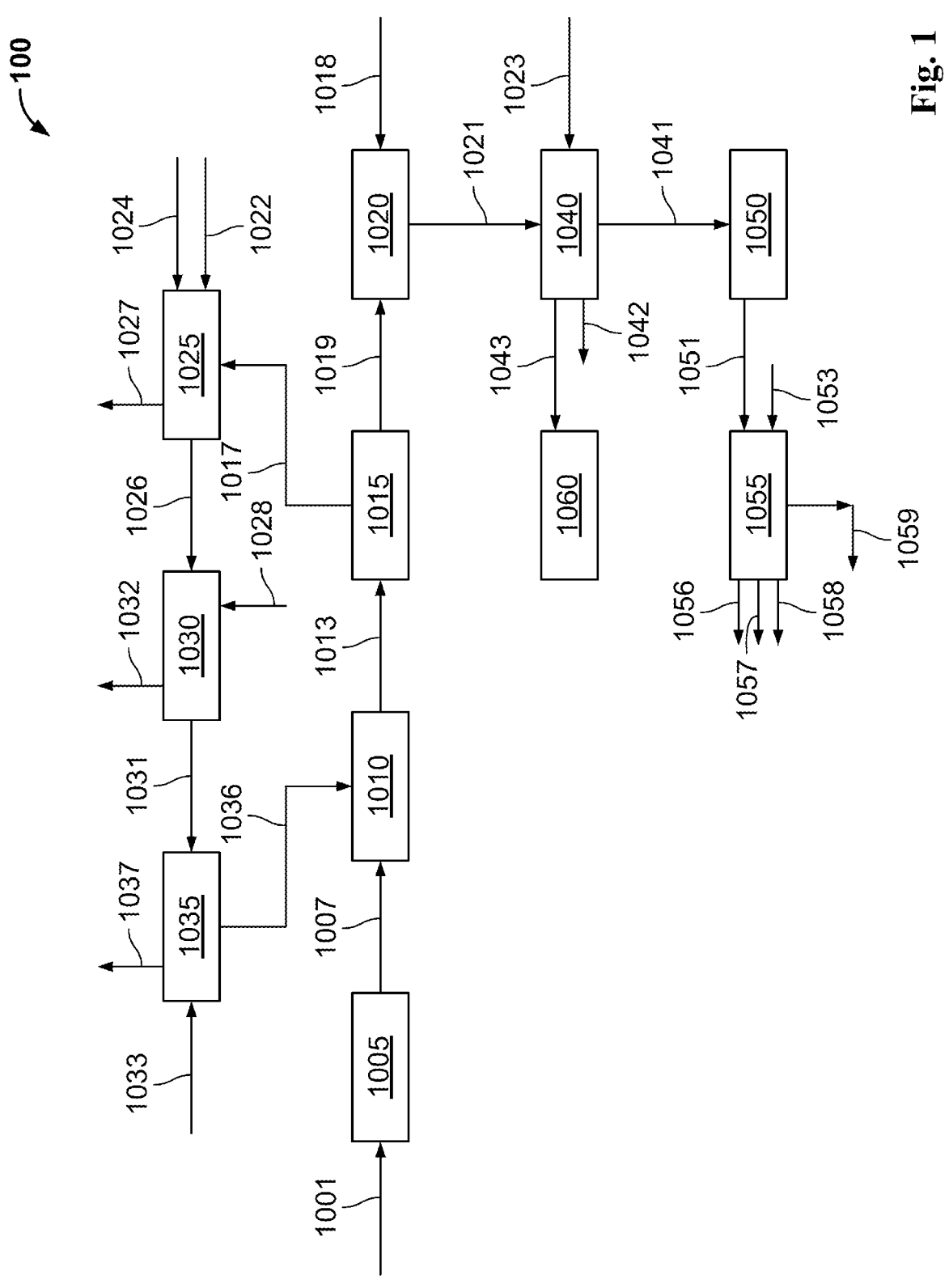
FIG. 1 depicts a system for dehydrogenating a hydrocarbon-containing feed, according to one or more embodiments described.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The terms "up" and "down"; "upward" and "downward"; "upper" and "lower"; "upwardly" and "downwardly"; "above" and "below"; and other like terms used herein refer to relative positions to one another and are not intended to denote a particular spatial orientation since the apparatus and methods of using the same may be equally effective at various angles or orientations.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16th Ed., John Wiley & Sons, Inc., (2016), Appendix V. For example, a Group 8 element includes Fe, a Group 9 element includes Co, and a group 10 element includes Ni. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula $$[Mg_{(1-x)}Al_x(OH)_2](A_{\frac{x}{n}}^{n-})\cdot mH_2O],$$

where A is a counter anion of a negative charge n, x is in a range of from >0 to <e1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. Yield (carbon mole basis) is conversion times selectivity.

The term "plenum" means a region of a reactor or separator that facilitates fluid communication between pipes or ducts carrying a hot product stream from a reactor or a separator to an outlet. A reactor or separator can have multiple plenums, e.g., a first plenum and a second plenum, and the term plenum will refer to any of the multiple plenums unless otherwise noted.

The term "slurry" means any liquid stream containing fines or solids in an amount of up to 20 wt % based on the weight of the slurry. The term "sludge" means any liquid stream containing fines or solids in a range from >20 wt % to 40 wt % based on the weight of the slurry. The term "cake" means any liquid stream containing fines or solids in an amount of >40 wt % based on the weight of the slurry.

Overview

A hydrocarbon-containing feed can be contacted with fluidized dehydrogenation catalyst particles in any suitable conversion zone to effect dehydrogenation of at least a portion of the hydrocarbon-containing feed to produce a conversion effluent that can include coked catalyst particles and one or more dehydrogenated hydrocarbons. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof. In some embodiments, the one or more dehydrogenated hydrocarbons can be or can include ethylene, propylene, one or more butenes, one or more pentenes, or any mixture thereof. In some embodiments, the conversion effluent can also include benzene.

The hydrocarbon-containing feed can contact the catalyst particles at a weight hourly space velocity in a range from 0.1 $hr^{-1}$ to 1,000 $hr^{-1}$, based on the weight of any $C_2$-$C_{16}$ alkanes and any $C_8$-$C_{16}$ aromatic hydrocarbons in the hydrocarbon-containing feed. A weight ratio of the fluidized dehydrogenation catalyst particles to a combined amount of any $C_2$-$C_{16}$ alkanes and any $C_8$-$C_{16}$ aromatic hydrocarbons can be in a range from 3 to 100. The hydrocarbon-containing feed and the catalyst particles can be contacted at a temperature in a range from 600° C. to 750° C.

A first particle stream rich in the coked catalyst particles and a first gaseous stream rich in the one or more dehydrogenated hydrocarbons can be separated or otherwise obtained from the conversion effluent. In some embodiments, the first particle stream and the first gaseous stream can be separated from the conversion effluent within one or more separation devices or gas/solid separators. In some embodiments, the first particle stream and the first gaseous stream can be separated from the conversion effluent via one or more cyclones. In some embodiments, the first particle stream and the first gaseous stream can be separated from the conversion effluent in a primary separation device and a secondary separation device downstream of and in fluid communication with the primary separation device, e.g., a primary cyclone and a secondary cyclone. In some embodiments, the first particle stream and the first gaseous stream can be separated from the conversion effluent in a primary separation device.

In some embodiments, at least a portion of the coked catalyst particles in the first particle stream can be contacted with an oxidant and a fuel in a combustion zone to effect combustion of at least a portion of the coke to produce a combustion effluent that can include catalyst particles lean in coke and a combustion gas. In such embodiment, a portion of the heat needed to produce the catalyst particles lean in coke is provided by combustion of the fuel. In other embodiments, at least a portion of the coked catalyst particles in the first particle stream can be contacted with an oxidant in a combustion zone to effect combustion of at least a portion of the coke to produce a combustion effluent that can include catalyst particles lean in coke and a combustion gas. In such embodiment, any hydrocarbon present within the combustion zone can be from entrained hydrocarbons from the conversion effluent. In other words, in such embodiment, no supplemental fuel is introduced into the combustion zone. Rather, a portion of the heat needed to produce the catalyst particles lean in coke can be provided by an electrical heater or other heating device. In both embodiments that use the fuel or the electrical heater, respectively, to provide a portion of the heat needed to produce the catalyst particles lean in coke, a dehydrogenation activity of the catalyst particles lean in coke can be less than a dehydrogenation activity of the coked catalyst particles.

A second particle stream rich in the catalyst particles lean in coke and a second gaseous stream rich in the combustion gas can be separated from the combustion effluent. In some embodiments, the second particle stream and the second gaseous stream can be separated from the combustion effluent within one or more separation devices or gas/solid separators. In some embodiments, the second particle stream and the second gaseous stream can be separated from the combustion effluent via one or more cyclones, e.g., one, two, three, four, or more cyclones connected in series. In some embodiments, the second particle stream and the second gaseous stream can be separated from the combustion effluent in a primary separation device and a secondary separation device downstream of and in fluid communication with the primary separation device, e.g., a primary cyclone and a secondary cyclone. In some embodiments, the second particle stream and second first gaseous stream can be separated from the combustion effluent in a primary separation device. In some embodiments, the combustion zone can include a dense fluidized bed operating in a bubbling regime, a turbulent regime, or a fast fluidization regime. In such embodiments, the second particle stream rich in the catalyst particles lean in coke can be withdrawn from the dense bed.

In some embodiments, when the fuel is introduced into the combustion zone, at least a portion of the catalyst particles lean in coke in the second particle stream can be contacted with an oxidative gas in an oxygen soak zone for a duration or period of time to produce conditioned catalyst particles that can have a dehydrogenation activity that is less than the dehydrogenation activity of the coked catalyst particles. In some embodiments, when the fuel is introduced into the combustion zone, at least a portion of the catalyst particles lean in coke in the second particle stream can be contacted with the oxidative gas in the oxygen soak zone at an oxidizing temperature in a range from 620° C. to 1,000° C. for a duration of at least 30 seconds to produce the conditioned catalyst particles. In some embodiments, when no supplemental fuel is introduced into the combustion zone and the electrical heater is used to provide heat therein, the catalyst particles lean in coke in the second particle stream can avoid being contacted with the oxidative gas in the oxygen soak zone.

In some embodiments, at least a portion of the conditioned catalyst particles can be contacted with a reducing gas in a reduction zone to produce regenerated catalyst particles having a dehydrogenation activity that is greater than the coked catalyst particles. In other embodiments, when no supplemental fuel is introduced into the combustion zone and the electrical heater is used to provide heat therein, at least a portion of the catalyst particles lean in coke in the second particle stream can be contacted with the reducing gas in the reduction zone to produce regenerated catalyst particles having a dehydrogenation activity that is greater than the dehydrogenation activity of the coked catalyst particles. It has been discovered that the catalyst particles disclosed herein exhibit improved activity and selectivity after undergoing the reduction step prior to recontact with an additional quantity of the hydrocarbon-containing feed. Additionally, the post-reduced catalyst particles may maintain the improved activity and selectivity for 10 minutes or more in the presence of the hydrocarbon-containing feed.

In some embodiments, the first gaseous stream rich in the dehydrogenated hydrocarbon(s) can be cooled to produce a cooled gaseous stream. At least a portion of the cooled gaseous stream can be compressed to produce a compressed gaseous stream. A plurality of products can be separated from the compressed gaseous stream.

Hydrocarbon Dehydrogenation Process

The hydrocarbon-containing feed can be contacted with the dehydrogenation catalyst particles within any suitable conversion zone to effect dehydrogenation of at least a portion of the hydrocarbon-containing feed to produce the conversion effluent that can include the coked catalyst particles and the one or more dehydrogenated hydrocarbons. In some embodiments, the conversion effluent can also include benzene. In some embodiments, the dehydrogenation catalyst particles can include a Group 8-10 element disposed on a support. In some embodiments, the hydrocarbon-containing feed and the dehydrogenation catalyst particles can be contacted in a conversion zone disposed within a continuous type of process commonly employed in fluidized bed reactors. In some embodiments, the conversion zone can be disposed within a riser reactor. In other embodiments, the conversion zone can be disposed within a downer reactor. In still other embodiments, the conversion zone can be disposed within a vortex reactor. In other embodiments, the conversion zone can be disposed within a reactor and can allow the fluidized dehydrogenation catalyst particles to form a relatively dense turbulent or fast fluidized bed therein during contact with the hydrocarbon-containing feed. A relatively dense turbulent or fast fluidized bed refers to a fluidized bed that is at a superficial gas velocity above the transition velocity designated as the critical velocity between the transition of a bubbling and turbulent bed, but below the transport velocity that demarcates a pneumatic transport regime in which the dehydrogenation catalyst particles are conveyed such as in a riser reactor. In other embodiments, the conversion zone can be disposed with a dehydrogenation reactor that includes a lower section operating as a fast fluidized or turbulent bed, and an upper section operating as a riser, where the average catalyst flow and the average gas flow are concurrently upward. In other embodiments, the conversion zone and the combustion zone can be located within a retrofitted fluidized catalytic cracking reactor-regenerator unit. The retrofitted fluidized catalytic cracking reactor-regenerator unit can have previously been used to carry out a fluidized catalytic cracking process that has been modified for use in the dehydrogenation process described herein. For example, the oxygen soaking zone and reducing zone can be incorporated into the fluidized catalyst cracking reactor-regenerator to provide a suitable retrofitted fluidized catalytic cracking unit.

Any number of reactors can be operated in series and/or in parallel. Any two or more types of reactors can be used in combination with one another. If two or more reactors are used the reactors can be operated at the same conditions and/or different conditions and can receive the same hydrocarbon-containing feed or different hydrocarbon-containing feeds. If two or more reactors are used the reactors can be arranged in series, in parallel, or a combination thereof with respect to one another. In some embodiments, suitable reactors can be or can include, but are not limited to, high gas velocity riser reactors, high gas velocity downer reactors, vortex reactors, reactors having a relatively dense fluidized catalyst bed at a first or bottom end and relatively less dense fluidized catalyst within a riser located at a second or top end, multiple riser reactors and/or downer reactors operated in parallel and/or series operating at the same or different conditions with respect to one another, or combinations thereof.

In some embodiments, the dehydrogenation catalyst particles can be pneumatically moved through the reaction system, e.g., fed into the conversion zone, fed into the combustion zone, fed into the oxygen soak zone (if such step is needed), fed into the reduction zone, transported through conduits connecting two or more locations, and the like, via a carrier fluid or transport fluid. The transport fluid can be or can include, but is not limited to, a diluent, one or more of the reactants in gaseous form, i.e., the one or more $C_2$-$C_{16}$ alkanes, the one or more $C_8$-$C_{16}$ alkyl aromatic hydrocarbons, the one or more dehydrogenated hydrocarbons, or a mixture thereof. Suitable transport fluids can be or can include, but are not limited to, molecular nitrogen, volatile hydrocarbons such methane, ethane, and/or propane, argon, carbon monoxide, carbon dioxide, steam, and the like. The amount of transport fluid can be sufficient to maintain the dehydrogenation catalyst particles in a fluidized state and to transport the dehydrogenation catalyst particles from one location, e.g., the combustion zone, to a second location, e.g., the conversion zone. In some embodiments, a weight ratio of the dehydrogenation catalyst particles to the transport fluid can be in a range from 5, 10, 15, or 20 to 50, 60, 80, 90, or 100. Injection points for the transport fluid, as can be made at multiple points along any one or more transfer lines that connect any two zones or other locations such as the combustion zone and the conversion zone.

The hydrocarbon-containing feed and dehydrogenation catalyst particles can be contacted at a temperature in a range from 300° C., 350° C., 400° C., 450° C., 500° C., 550° C., 600° C., 620° C., 630° C., 640° C., 650° C., 660° C., 670° C., 680° C., 690° C., or 700° C. to 725° C., 750° C., 760° C., 780° C., 800° C., 825° C., 850° C., 875° C., or 900° C. In some embodiments, the hydrocarbon-containing feed and dehydrogenation catalyst particles can be contacted at a temperature of at least 620° C., at least 630° C., at least 640° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C.

In some embodiments, the hydrocarbon-containing feed can be introduced into the conversion zone and contacted with the dehydrogenation catalyst particles therein for a duration or time period of ≤5 hours, ≤4 hours, ≤3 hours, ≤1 hour, ≤0.5 hours, ≤0.1 hours, ≤3 minutes, ≤1 minute, ≤30 seconds, or ≤0.1 second. In other embodiments, the hydrocarbon-containing feed can be introduced into the conversion zone and contacted with the dehydrogenation catalyst particles therein for a time period in a range from 0.1 seconds, 1 second, 1.5 seconds, 2 seconds, or 2.5 seconds to 3 seconds, 5 seconds, 10 seconds, 20 seconds, 30 seconds, 45 seconds, 1 minute, 1.5 minutes, 2 minutes, 2.5 minutes, or 3 minutes. In some embodiments, the average residence time of the dehydrogenation catalyst particles within the conversion zone can be ≤7 minutes, ≤6 minutes, ≤5 minutes, ≤4 minutes≤3 minutes, ≤2 minutes, ≤1.5 minutes, ≤1 minute, ≤45 seconds, ≤30 seconds, ≤20 seconds, ≤15 seconds, ≤10 seconds, ≤7 seconds, ≤5 seconds, ≤3 seconds, ≤2 seconds, or ≤1 second. In some embodiments, the average residence time of the dehydrogenation catalyst particles within the conversion zone can be greater than an average residence time of the gaseous components, e.g., the hydrocarbon-containing feed and the conversion effluent obtained therefrom within the conversion zone.

The hydrocarbon-containing feed and the dehydrogenation catalyst particles can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. In some embodiments, the hydrocarbon partial pressure during contact of the hydrocarbon-containing feed and the dehydrogenation catalyst particles can be in a range from 20 kPa-absolute, 50 kPa-absolute, 100 kPa-absolute, 150 kPa, 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. In some embodiments, the hydrocarbon-containing feed and dehydrogenation catalyst particles can be contacted under a single $C_2$-$C_{16}$ alkane, e.g., propane, pressure of at least 20 kPa-absolute, at least 50 kPa-absolute, at least 70 kPa-absolute, at least 100 kPa-absolute, at least 150 kPa-absolute, or at least 250 kPa-absolute to 300 kPa-absolute, 400 kPa-absolute, 500 kPa-absolute, or 1,000 kPa-absolute.

The hydrocarbon-containing feed can be contacted with the dehydrogenation catalyst particles within the conversion zone at any weight hourly space velocity (WHSV) effective for carrying out the dehydrogenation process. In some embodiments, the WHSV can be 0.1 hr$^{-1}$, 0.2 hr$^{-1}$, 0.4 hr$^{-1}$, 0.8 hr$^{-1}$, 2 hr$^{-1}$, 4 hr$^{-1}$, or 8 hr$^{-1}$ to 16 hr$^{-1}$, 32 hr$^{-1}$, 64 hr$^{-1}$, 100 hr$^{-1}$, 250 hr$^{-1}$, 500 hr$^{-1}$, 750 hr$^{-1}$, or 1,000 hr$^{-1}$. In some embodiments, a ratio of the dehydrogenation catalyst particles to a combined amount of any $C_2$-$C_{16}$ alkanes and any $C_8$-$C_{16}$ alkyl aromatic hydrocarbons can be in a range from 1, 3, 5, 10, 15, 20, 25, 30, or 40 to 50, 60, 70, 80, 90, 100, 110, 125, or 150 on a weight to weight basis.

In some embodiments, at least a portion of the fluidized dehydrogenation catalyst particles within the conversion zone can be removed, fed into a heat input device where the dehydrogenation catalyst particles can be heated, and the heated catalyst particles can be fed back into the conversion zone. With the reactions occurring within the conversion zone being endothermic, it can be beneficial to remove a portion of the fluidized dehydrogenation catalyst particles therefrom to further increase the temperature after some contact with the hydrocarbon-containing feed. The heat can be indirectly transferred from any suitable heat transfer medium, provided via an electric heater, or any other suitable heater typically used to indirectly heat catalyst particles. In another embodiment, heat can be applied within the conversion zone directly.

In some embodiments, the hydrocarbon-containing feed, prior to introduction into the conversion zone, can optionally be subjected to one or more pre-treatment processes. In some embodiments, the hydrocarbon-containing feed can be pre-heated to a temperature of up to ≤620° C. and introduced into the conversion zone at or near the pre-heated temperature. In some embodiments, the hydrocarbon-containing feed can be treated to remove at least a portion of any sulfur compounds, at least a portion of any nitrogen compounds, at least a portion of any methane, at least a portion of any $C_2$ hydrocarbons, at least a portion of any $C_{4+}$ hydrocarbons, or any combination thereof to produce a pre-treated hydrocarbon-containing feed that can be introduced into the conversion zone. In other embodiments, the hydrocarbon-containing feed can be treated by adding one or more additives thereto such as one or more sulfur compounds to produce a pre-treated hydrocarbon-containing feed that can be introduced into the conversion zone.

The first particle stream rich in the coked catalyst particles and lean in the one or more dehydrogenated hydrocarbons and the first gaseous stream rich in the one or more dehydrogenated hydrocarbons can be separated or otherwise obtained from the conversion effluent via any suitable apparatus. In some embodiments, the first particle stream and the first gaseous stream can be obtained from the conversion effluent via one or more solid-gas impingement separators, e.g., one or more cyclone separators. In some embodiments, the cyclone separator can be or can include a two staged or "coupled" configuration including both positive and negative pressure configurations. In some embodiments, suitable cyclone separators can include those disclosed in U.S. Pat. Nos. 4,502,947; 4,985,136; and 5,248,411. In other embodiments, the first particle stream and the first gaseous stream can be obtained from the conversion effluent via a "T" shaped conduit that can cause a majority of the coked catalyst particles to flow in one direction via gravity and the gaseous components to flow in the other direction.

In some embodiments, the first gaseous stream rich in the one or more dehydrogenated hydrocarbons can also include entrained coked catalyst particles. In such embodiments, the first particle stream rich in the coked catalyst particles and lean in the one or more dehydrogenated hydrocarbons can include >95%, >96%, >97%, >98%, or >99%, >99.9%, >99.99% of the dehydrogenation catalyst particles in the conversion effluent. As such, in some embodiments, the first gaseous stream rich in the one or more dehydrogenated hydrocarbons can include entrained coked catalyst particles in an amount of >0.001%, >0.005%, >0.01%, >0.05%, >0.1%, >0.5%, >1%, or >1.5% to 3%, 4%, or 5% of the dehydrogenation catalyst particles in the conversion effluent.

In some embodiments, at least a portion of the coked catalyst particles in the first particle stream can be contacted with one or more oxidants and, optionally, one or more hydrocarbon fuels in a combustion zone to effect combustion of at least a portion of the coke and, if present, the fuel to produce a combustion effluent that can include catalyst particles lean in coke and a combustion gas. In other embodiments, at least a portion of the coked catalyst particles in the first particle stream can be contacted with one or more oxidants in the absence of any supplemental fuel in a combustion zone to effect combustion of at least a portion of the coke to produce the combustion effluent that can include catalyst particles lean in coke and a combustion gas. In some embodiments, when the supplemental fuel is not introduced into the combustion zone, an electrical heater or other heating device can be used to provide heat to the combustion zone. When fuel is used, in some embodiments, the combustion zone can include a riser where the average catalyst flow and average gas flow can be concurrently upward. In some embodiments, the combustion zone can include a lower section operating as a fast fluidized, turbulent, or bubbling bed, and an upper section operating as a riser, where the average catalyst flow and average gas flow can be concurrently upward. In some embodiments, the combustion zone can include a fast fluidized, turbulent, or bubbling bed, where the average catalyst flow can be downward and the average gas flow can be upward. The soaking zone can occur in a fast fluidized, turbulent or bubbling bed reactor, where the average catalyst flow can be downward and the average gas flow can be upward. The separation of the catalyst particles lean in coke entrained in the combustion gas moving upward and the separation of the conditioned catalyst particles entrained in the oxidative gas moving upward can occur within the same set of separation devices. When no fuel is used, the combustion zone can also function as the oxygen soaking zone described above. In some embodiments, the arrangement of the oxygen soaking zone and the combustion zone relative to one another can be the same or similar to how the oxygen soaking zone and the combustion zone are arranged and described in U.S. Pat. Nos. 10,647,634 and 10,688,477, and WO Publication No.: WO2020/263544.

The oxidant can be or can include, but is not limited to, molecular oxygen, ozone, carbon dioxide, steam, or a mixture thereof. In some embodiments, an amount of oxidant in excess of that needed to combust 100% of the coke on the coked catalyst particles can be used to increase the rate of coke removal from the catalyst particles, so that the time needed for coke removal can be reduced and lead to an increased yield in the upgraded product produced within a given period of time. The optional fuel can be or can include, but is not limited to, molecular hydrogen, methane, ethane, propane, liquefied petroleum gas, or a mixture thereof. The optional fuel can be mixed with an inert gas such as argon, neon, helium, molecular nitrogen, methane, or a mixture thereof.

The coked catalyst particles and oxidant and, if present, the fuel can be contacted with one another at a temperature in a range from 500° C., 550° C., 600° C., 650° C., 700° C., 750° C., or 800° C. to 900° C., 950° C., 1,000° C., 1,050° C., or 1,100° C. to produce the combustion effluent. In some embodiments, the coked catalyst particles and oxidant and, if present, the fuel can be contacted with one another at a temperature in a range from 500° C. to 1,100° C., 600° C. to 1,100° C., 600° C. to 1,000° C., 650° C. to 950° C., 700° C. to 900° C., or 750° C. to 850° C. to produce the combustion effluent. The coked catalyst particles and oxidant and, if present, the fuel can be contacted with one another under an oxidant partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute to produce the combustion effluent.

The coked catalyst particles and oxidant and, if present, the fuel can be contacted with one another for a time period in a range from 0.1 seconds, 0.5 seconds, 1 second, 3 seconds, 5 seconds, 10 seconds, 15 seconds, 30 seconds, 1 minute, 2 minutes, or 5 minutes to 10 minutes, 20 minutes, 30 minutes, 40 minutes, 50 minutes, or 60 minutes. For example, the coked catalyst particles and oxidant and, if present, the fuel can be contacted with one another for a time period in a range from 0.5 seconds to 50 minutes, 55 minutes, or 60 minutes. In some embodiments, the coked catalyst particles and oxidant and, if present, the fuel can be contacted for a time period sufficient to remove ≥50 wt %, ≥75 wt %, or ≥90 wt % or >99% of any coke disposed on the catalyst particles.

In some embodiments, the time period the coked catalyst particles and oxidant and, if present, the fuel contact one another can be greater than the time period the catalyst particles contact the hydrocarbon-containing feed to produce the conversion effluent. For example, the time period the coked catalyst particles and oxidant and, if present, the fuel contact one another can be at least 50%, at least 100%, at least 300%, at least 500%, at least 1,000%, at least 10,000%, at least 30,000%, at least 50,000%, at least 75,000%, at least 100,000%, at least 250,000%, at least 500,000%, at least 750,000%, at least 1,000,000%, at least 1,250,000%, at least 1,500,000%, at least 1,800,000%, at least 2,500,000%, at least 3,500,000%, or 4,140,000% greater than the time period the catalyst particles contact the hydrocarbon-containing feed to produce the conversion effluent.

Without wishing to be bound by theory, it is believed that at least a portion of the metal element, e.g., a Group 8-10 element such as Pt, disposed on the support in the coked catalyst particles can be agglomerated as compared to the catalyst particles prior to contact with the hydrocarbon-containing feed. It is believed that during combustion of at least a portion of the coke on the coked catalyst particles that at least a portion of the metal element, e.g., a Group 8-10 element, can be re-dispersed about the support. Re-dispersing at least a portion of any agglomerated metal element, e.g., a Group 8-10 element, can increase the dehydrogenation activity and improve the stability of the catalyst particles over many cycles.

In some embodiments, at least a portion of the catalyst particles lean in coke in the second particle stream can be contacted with an oxidative gas in an oxygen soak zone to produce conditioned catalyst particles. Preferably, the catalyst particles lean in coke in the second particle stream can be contacted with the oxidative gas in the oxygen soak zone when the fuel is introduced into the combustion zone. When the fuel is not introduced into the combustion zone and an electrical or other heating device is used to provide heat thereto, the catalyst particles lean in coke in the second particle stream can be sent straight to a reduction zone discussed in more detail below and, as such, do not need to be subjected to contact with the oxidative gas. It should be understood, however, that when the fuel is not introduced into the combustion zone the catalyst particles lean in coke in the second particle stream can also be contacted with the oxidative gas in the oxygen soak zone if so desired. It should also be understood that when the fuel is not introduced into the combustion zone, the combustion zone and the oxygen soak zone can be combined into a single zone for both coke combustion and oxygen soak, and a single oxidative gas can be used for both coke combustion and oxygen soak. In such embodiment, the terms "catalyst particles lean in coke" and "the conditioned catalyst particles" refer to the same catalyst particle stream.

In some embodiments, the catalyst particles lean in coke in the second particle stream can be contacted with the oxidative gas at an oxidizing temperature in a range from 620° C., 650° C., 675° C., 700° C., or 750° C. to 800° C., 850° C., 900° C., 950° C., or 1,000° C. to produce the conditioned catalyst particles. In some embodiments, the catalyst particles lean in coke in the second particle stream can be contacted with the oxidative gas for a duration or time period in a range from 20 seconds, 30 seconds, 1 minute, 2 minutes, 3 minutes, or 5 minutes to 10 minutes, 15 minutes, 20 minutes, 25 minutes, 30 minutes, 40 minutes, 50 minutes, or 60 minutes to produce the conditioned catalyst particles. The conditioned catalyst particles can have a dehydrogenation activity that is less than the dehydrogenation activity of the coked catalyst particles. In some embodiments, the oxidative gas introduced into the oxygen soak zone can include ≤5 mol %, ≤3 mol %, ≤1 mol %, ≤0.5 mol %, or ≤0.1 mol % of $H_2O$. The contact between the oxidative gas and the catalyst particles lean in coke in the second particle stream can also be referred to as "dry air soaking". It should be understood that the oxidative gas and any other gaseous components within the oxygen soak zone includes ≤5 mol %, ≤3 mol %, ≤1 mol %, ≤0.5 mol %, or ≤0.1 mol % of $H_2O$.

It has been surprisingly and unexpectedly discovered that contacting the catalyst particles lean in coke produced in the presence of the optional fuel with the oxidative gas that includes no greater than 5 mol % of $H_2O$ can significantly improve the activity and/or selectivity of the regenerated catalyst produced via contact with the reducing gas discussed in more detail below. Without wishing to be bound by theory, it is believed that $H_2O$ present in the oxidative gas or produced as a combustion product may significantly reduce the effectiveness of the re-dispersion of the Group 8-10 element, e.g., Pt, and hence the effectiveness of the regenerated catalyst.

In some embodiments, when no fuel is introduced into combustion zone, at least a portion of the catalyst particles lean in coke in the second particle stream or when fuel is introduced into the combustion zone at least a portion of the conditioned catalyst particles can be contacted with a reducing gas in a reduction zone to produce regenerated catalyst particles. Suitable reducing gases (reducing agent) can be or can include, but are not limited to, molecular hydrogen, carbon monoxide, methane, ethane, ethylene, propane, propylene, steam, or a mixture thereof. In some embodiments, the reducing gas can be mixed with an inert gas such as argon, neon, helium, molecular nitrogen, or a mixture thereof. In such embodiments, at least a portion of the metal element, e.g., a Group 8-10 element, in the regenerated catalyst particles can be reduced to a lower oxidation state, e.g., the elemental state, as compared to the metal element, e.g., a Group 8-10 element, in the catalyst particles lean in coke in the second particle stream (when no fuel is introduced into the combustion zone) and as compared to the metal element in the conditioned catalyst particles.

In some embodiments, the catalyst particles lean in coke in the second particle stream or the conditioned catalyst particles and the reducing gas can be contacted at a temperature in a range from 400° C., 450° C., 500° C., 550° C., 600° C., 620° C., 650° C., or 670° C. to 720° C., 750° C., 800° C., or 900° C. The catalyst particles lean in coke in the second particle stream or the conditioned catalyst particles and the reducing gas can be contacted for a duration or time period in a range from 0.1 seconds, 1 second, 2 seconds, 5 seconds, 10 seconds, 20 seconds, 30 seconds, 60 seconds, or 75 seconds to 100 seconds, 200 seconds, 300 seconds, 600 seconds, or 1,000 seconds, or 1,800 seconds. The catalyst particles lean in coke in the second particle stream or the conditioned catalyst particles and reducing gas can be contacted at a reducing gas partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute.

In some embodiments, a first portion of the coked catalyst particles in the first particle stream rich in the coked catalyst particles can be fed into the combustion zone for combustion of the coke disposed thereon and a second portion of the coked catalyst particles in the first particle stream can be recycled directly back into the conversion zone. In some embodiments, a first portion of the coked catalyst particles in the first particle stream rich in the coked catalyst particles can be fed into the combustion zone for combustion of the coke disposed thereon, and a second portion of the coked catalyst particles can be fed into the reduction zone. In other embodiments, a first portion of the coked catalyst particles in the first particle stream rich in the coked catalyst particles can be fed into the combustion zone for combustion of the coke disposed thereon, a second portion of the coked catalyst particles can be recycled directly back into the conversion zone, and a third portion of the coked catalyst particles can be fed into the reduction zone. In other embodiments, a first portion of the coked catalyst particles in the first particle stream rich in the coked catalyst particles can be fed into the combustion zone for combustion of the coke disposed thereon, a second portion of the coked catalyst particles can be recycled directly back into the conversion zone, a third portion of the coked catalyst particles can be fed into the oxygen soak zone, and a fourth portion of the coked catalyst particles can be fed into the reduction zone. In any of these embodiments, on a continuous basis or intermittent basis, a portion of the coked catalyst particles, a portion of the catalyst particles in the second particle stream, a portion of the conditioned catalyst particles, and/or a portion of the regenerated catalyst particles can be removed from the process and new or make-up catalyst particles can be introduced into the process. The removal of catalyst particles can be done as the catalyst particles break down in size, become inactivated, and/or begin to convert the hydrocarbon-containing feed at an undesirable rate of conversion. In some embodiments, at least a portion of any removed catalyst particles can be conveyed to a metal reclamation facility for metal recovery therein.

At least a portion of the coked catalyst particles, at least a portion of the catalyst particles lean in coke in the second particle stream, at least a portion of the conditioned catalyst particles, at least a portion of the regenerated catalyst particles, new or make-up catalyst particles, or any mixture thereof can be contacted with an additional quantity of the hydrocarbon-containing feed within the conversion zone to produce additional conversion effluent and re-coked catalyst particles. In some embodiments, the cycle time from the contacting the hydrocarbon-containing feed with the catalyst particles to the contacting the additional quantity of the hydrocarbon-containing feed with at least a portion of the regenerated particles can be ≤5 hours, ≤4 hours, ≤3 hours, ≤2 hours, ≤70 minutes, ≤60 minutes, ≤45 minutes, or ≤30 minutes, e.g., from 1 minute to 70 minutes or 5 minutes to 45 minutes.

In some embodiments, one or more additional feeds, e.g., one or more stripping fluids, can be utilized to remove at least a portion of any entrained gaseous components from the catalyst particles. In some embodiments, the coked catalyst particles can be contacted with a stripping fluid prior to contact with the oxidant to remove at least a portion of any entrained upgraded hydrocarbons and/or molecular hydrogen, and/or other gaseous components. Similarly, the catalyst particles lean in coke in the second particle stream, the conditioned catalyst particles, and/or the regenerated catalyst particles can be contacted with a stripping gas to remove at least a portion of any entrained combustion gas, oxidative gas, or reducing gas therefrom. In some embodiments, the stripping gas can be inert under the dehydrogenation, combustion, and/or reducing conditions. Suitable stripping fluids can be or can include, but are not limited to, molecular nitrogen, helium, argon, carbon dioxide, steam, methane, or a mixture thereof. The stripping gas can be contacted with the coked catalyst particles, the regenerated catalyst particles, and/or the regenerated and reduced catalyst particles at a volume ratio of about 0.1 m³ to 10 m³ of stripping gas per cubic meter of catalyst particles.

As noted above, the first cycle begins upon contact of the catalyst particles with the hydrocarbon-containing feed, followed by contact with at least the oxidant and the reducing gas to produce the regenerated catalyst particles, and the first cycle ends upon contact of the regenerated catalyst particles with the additional quantity of the hydrocarbon-containing feed. If any sweep fluid is utilized, e.g., to strip residual hydrocarbons from the coked catalyst particles, the time period such sweep fluid is utilized would be included in the cycle time.

In one embodiment, a riser configuration can be implemented in which the hydrocarbon-containing feed can be admixed with a dilution gas and contacted with heated and fluidized catalyst particles within the riser. The dilution gas can be or can include, but is not limited to, molecular nitrogen, methane, steam molecular hydrogen, or a mixture thereof. The combined gas can convect or otherwise convey the fluidized catalyst particles through the riser while contacting and reacting as the mixture flows through the riser to produce the conversion effluent that includes the one or more dehydrogenated hydrocarbons and the coked catalyst particles. A residence time of the hydrocarbon-containing feed and the fluidized catalyst particles can be sufficient to achieve a desired conversion of the hydrocarbon-containing feed to the one or more dehydrogenated hydrocarbons. The specific design of the riser, including fabrication and dimensions, can be dependent, at least in part, on the intended chemistry, but typically can require velocities in excess of 4.5 m/s under average gas composition.

Systems suitable for carrying out the dehydrogenation of the hydrocarbon-containing feed can include systems that are well-known in the art such as the fluidized reactors disclosed in U.S. Pat. Nos. 3,888,762; 7,102,050; 7,195,741; 7,122,160; and 8,653,317; U.S. Patent Application Publication Nos. 2004/0082824; 2008/0194891; and WO Publication Nos. WO2001/85872; WO2004/029178; and WO2005/077867.

The first gaseous stream can be cooled to produce a cooled gaseous stream. In some embodiments, the first gaseous stream can be cooled via indirect heat exchange in one or more heat exchangers by transferring heat from the first gaseous stream to a heat transfer medium, by direct contact with a quench medium, or a combination thereof. In some embodiments, the first gaseous stream can be cooled via only indirect heat exchange to produce the cooled gaseous stream. In other embodiments, the first gaseous stream can be cooled via only direct contact with a quench medium. In other embodiments, the first gaseous stream can be cooled via both indirect heat exchange and by direct contact with a quench medium in either order or sequence.

In some embodiments, the first gaseous stream can be indirectly cooled by indirectly transferring heat to any suitable heat transfer medium. Suitable heat transfer mediums can be or can include, but are not limited to, the hydrocarbon-containing feed to produce a pre-heated hydrocarbon-containing feed that can be introduced into the conversion zone, water, steam, other hydrocarbon streams, or any combination thereof. Any suitable heat exchanger can be used to indirect transfer heat from the first gaseous stream to the heat transfer medium.

In some embodiments, the first gaseous stream can be contacted with a first quench medium to produce the cooled gaseous stream. For example, when the separation device or gas/solid separator is a cyclone, the first gaseous stream can be contacted with the first quench medium within a plenum of the cyclone. When a plurality of cyclones is used in series the first gaseous stream can be contacted with the first quench medium at any locations in-between or after the plurality of cyclones. In other embodiments, the first gaseous stream can be contacted within a transfer line in fluid communication with an exit of the separation device or gas/solid separator and a quench tower.

In some embodiments, the first quench medium can be in a gaseous phase, a liquid phase, or a gaseous phase and a liquid phase mixture when contacted with the first gaseous stream. In some embodiments, the first quench medium can be in liquid phase when contacted with the first gaseous stream and can be completely in a gaseous phase after contacting the first gaseous stream.

In some embodiments, the first gaseous stream can be at a temperature of ≥600° C., ≥620° C., ≥630° C., ≥640° C., ≥650° C., ≥660° C., ≥670° C., ≥680° C., or ≥700° C. when initially contacted with the first quench medium and/or when introduced into a heat exchanger for the indirect transfer of heat to a heat transfer medium. In some embodiments, the cooled gaseous stream can be at a temperature that is at least 10° C., at least 20° C., at least 30° C., at least 60° C., 80° C., or at least 100° C. less than the temperature of the first gaseous stream prior to contact with the first quench medium or prior to introduction into the heat exchanger. In some embodiments, the cooled gaseous stream can be at a temperature in a range from 500° C., 515° C., 530° C., 550° C., or 560° C. to 575° C., 590° C., 600° C., 610° C., or 620° C. In some embodiments, the cooled gaseous stream can be at a temperature of ≥500° C. or ≥550° C. to <620° C.

In some embodiments, the cooled gaseous stream can be contacted with a second quench medium within a contact zone disposed within a quench tower. In some embodiments, the second quench medium can be contacted counter-currently with the cooled gaseous stream within the quench tower. For example, the cooled gaseous stream can be introduced into the quench tower below the second quench medium and flow upwardly within the quench tower and the second quench medium can flow downwardly within the quench tower. In some embodiments, the second quench medium can be introduced into the quench tower via one or more nozzles.

As noted above, in some embodiments, the first gaseous stream can include entrained coked catalyst particles therein. In such embodiment, a third gaseous stream substantially free or free of the entrained coked catalyst particles that includes the one or more dehydrogenated hydrocarbons can be recovered as an overhead from the quench tower and a slurry stream that can include at least a portion of the second quench medium and the entrained coked catalyst particles can be recovered as a bottoms from the quench tower. In some embodiments, the entrained coked catalyst particles can interact more strongly with a liquid therefore the entrained coked catalyst particles can be entrained in the second quench medium if the second quench medium stays as a liquid. In some embodiments, the third gaseous stream substantially free of the entrained coked catalyst particles can include <10 wt %, <5 wt %, <3 wt %, <1 wt %, <0.5 wt %, <0.1 wt %, <0.01 wt %, or <0.001 wt % of any entrained coked catalyst particles. In some embodiments, the gaseous stream can be at a temperature in a range from 50° C., 100° C., or 150° C. to 200° C., 250° C., or 300° C.

When the first gaseous stream is directly contacted with the first quench medium, a condensed first quench medium stream can be recovered as a side draw from the quench tower and at least a portion of the condensed first quench medium can be recycled to contact an additional quantity of the first gaseous stream. In some embodiments, the condensed first quench medium recovered from the quench tower can be at a temperature in a range from 50° C., 60° C., or 70° C. to 80° C., 100° C., or 120° C.

When the first gaseous stream includes entrained catalyst particles, a slurry stream that can include at least a portion of the second quench medium and the entrained coked catalyst particles can be recovered as a bottoms stream from the quench tower. In some embodiments, a bottom zone within the quench tower can contain an inventory of the slurry stream such that the slurry stream recovered from the quench tower can be drawn from the inventory. The slurry stream can be at a temperature in a range from 150° C., 200° C., or 250° C. to 300° C., 400° C., or 500° C. when recovered from the quench tower.

In some embodiments, the quench tower can include one or more internal structures that can facilitate separation of the cooled gaseous stream into the third gaseous stream, the first quench medium stream (when used), and the slurry stream. Illustrative internal structures can include, but are not limited to, trays, grids, packing, or any combination thereof. Illustrative trays can include, but are not limited to, fixed valve trays, jet tab trays, sieve trays, dual flow trays, baffle trays, angle iron trays, draw off trays, shed deck trays, disk trays, donut trays, side by side-splash trays, or any combination thereof. Suitable fixed valve trays, sieve trays, dual flow trays, and grids can include those disclosed in Distillation Design, Henry Z. Kister, McGraw-Hill Inc., 1992, pages 262 to 265 and pages 464-466. Suitable jet tab trays can include those disclosed in WO Publication No. WO2011/014345.

In some embodiments, if the process conditions within the quench tower are such that entrained coked catalyst particles can remain in the third gaseous stream recovered as the overhead from the quench tower, the third gaseous stream can be subjected to further processing. In some embodiments, if the third gaseous stream recovered as the overhead from the quench tower includes any entrained coked catalyst particles, the third gaseous stream can be further separated via one or more electrostatic precipitators, one or more filters, one or more screens, one or more membranes, wet gas scrubber, contact with an absorbent scavenger, one or more additional quench towers, one or more electrocyclones, one or more hydrocyclones, one or more centrifuges, one or plates or cones, or any combination thereof to remove at least a portion of the entrained coked catalyst particles therefrom.

In some embodiments, if the hydrocarbon-containing feed includes water and/or water is produced during the dehydrogenation reaction such that the conversion effluent contains water, a water stream can be recovered from the quench tower as a second side draw from the quench tower. In such embodiment, the water stream can be removed from the process, a portion of the water stream can be recycled to an upper section of the quench tower to further facilitate separation of the entrained coked catalyst fines, first quench medium, and second quench medium from the cooled gaseous stream within the quench tower, or a combination thereof. In some embodiments, at least a portion of the water stream can also be vaporized and recycled to the inlet of the conversion zone as a co-feed for the hydrocarbon-containing feed.

The first quench medium and the second quench medium can independently be or can independently include, but are not limited to, one or more aromatic hydrocarbons, water, or a mixture thereof. In some embodiments, the aromatic hydrocarbon can be or can include benzene, one or more mono-substituted benzenes, one or more di-substituted benzenes, one or more poly-substituted benzenes, and/or one or more polyaromatic hydrocarbons having a normal boiling point of <580° C. In some embodiments, the polyaromatic hydrocarbon can have a normal boiling point of <580° C., <550° C., <500° C., <400° C., <300° C., <200° C., or <100° C. Suitable aromatic hydrocarbon can be or can include, but are not limited to, benzene, toluene, cumene, ethylbenzene, xylene, methylethylbenzene, trimethylbenzene, methyl-naphthalene, A-100 solvent mixture, A-150 solvent mixture, A-200 solvent mixture, A-250 solvent mixture, middle distillate, ultra-low sulfur diesel, heavy gas oil, or any mixture thereof.

In some embodiments, the second quench medium can have a low surface tension, high thermostability, and low toxicity. In some embodiments, the first quench medium can be or can include, but is not limited to, benzene and the second quench medium can be or can include, but is not limited to, A-100 solvent mixture, A-150 solvent mixture, A-200 solvent mixture, A-250 solvent mixture, middle distillate, ultra-low sulfur diesel, heavy gas oil, or any mixture thereof.

In some embodiments, a composition of the first quench medium and a composition of the second quench medium can be the same or different. In some embodiments, a composition of the first quench medium and the second quench medium can include one or more components that are the same and one or more components that are different such that a portion of the compositions of the first and second quench mediums are the same and a portion of the compositions of the first and second quench mediums are different. In some embodiments, the second quench medium can have a normal boiling point that is greater than a normal boiling point of the first quench medium. In some embodiments, the second quench medium can have a normal boiling point that is lower than a normal boiling point of the first quench medium. In some embodiments, the first quench medium can be or can include benzene and the second quench medium can include one or more polyaromatic hydrocarbons. In some embodiments, the first quench medium and/or the second quench medium may not be used.

In some embodiments, a weight ratio of the first quench medium to the first gaseous stream can be in a range from 0.01, 0.05, or 0.08 to 0.1, 0.2, or 0.3. In some embodiments, a weight ratio of the second quench medium to the cooled gaseous stream can be in a range from 0.01, 0.1, or 0.3 to 0.5, 1, 2, or 5. In some embodiments, a weight ratio of the first quench medium to the second quench medium can be in a range from 0.002, 0.02, or 0.2 to 1, 5, or 10.

When the first gaseous stream includes entrained coked catalyst particles, at least a portion of the entrained coked catalyst particles can be separated from the slurry to provide a recovered second quench medium lean or free of any entrained coked catalyst particles and a recovered entrained coked catalyst particles stream. In some embodiments, at least a portion of the recovered second quench medium can be recycled to the quench tower to contact an additional quantity of the first cooled gaseous stream therein.

In some embodiments, the entrained coked catalyst particles can be separated from the slurry via one or more liquid/solid separation devices. Suitable liquid/solid separation devices can be or can include, but are not limited to, one or more filters, one or more membranes, one or more screens, one or more centrifuges, one or more settling tanks, or any combination thereof. In some embodiments, two or more liquid/solid separation devices can be used in parallel such that at least one first liquid/solid separation device can be operated in a filtration mode while at least one second liquid/solid separation device can be operated in a back-washing mode to remove collected coked catalyst particles therefrom. The filtration and backwashing modes can be periodically alternated. In some embodiments, when two or more filters are used to separate the entrained coked catalyst particles from the slurry the backwashing mode can include at least one compressed gas pulse through the at least one filter that is in the backwashing mode in the reverse flow direction to remove the separated coked catalyst particles therefrom. In some embodiments, a combustion or flue gas recovered from the combustion zone can be used as the gas for backwashing the filters. In some embodiments, a liquid stream can be used for backwashing the filters. In some embodiments, a suitable process for recovering the entrained coked catalyst particles from the slurry can include the process disclosed in U.S. Pat. No. 7,375,143.

In some embodiments, at least a portion of the cooled first gaseous stream, e.g., the third gaseous stream that can be recovered from the quench tower, can be compressed to produce a compressed gaseous stream. The at least a portion of the cooled first gaseous steam can be compressed in one or more compressors or compression stages to produce the compressed gaseous stream. A plurality of products can be separated from the compressed gaseous stream. The compressed gaseous stream can be introduced into a product recovery zone or unit that can separate a plurality of products therefrom. The product recovery unit can be or can include, but is not limited to, any one or more of the following: distillation column, membrane separation, adsorption bed, cryogenic separations.

In some embodiments, the compressed gaseous stream can be separated within the product recovery zone into a light gas stream, an unreacted hydrocarbon-containing feed stream, a dehydrogenated hydrocarbon stream, and a liquid stream. In some embodiments, the light gas stream can include hydrogen, methane, butane, or any mixture thereof. In some embodiments, at least a portion of the light hydrocarbon stream can be introduced into the combustion zone as the optional fuel. The unreacted hydrocarbon-containing feed, e.g., ethane, propane, can be recycled to the conversion zone. The dehydrogenated hydrocarbon stream can be further processed to produce one or more products such as polyethylene, polypropylene, or other polymers. The liquid stream or at least a portion thereof can be used as the first quench medium, the second quench medium, or a combination thereof. In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: oxygenates such as methyl tert-butyl ether, fuel additives such as diisobutene, synthetic elastomeric polymer such as butyl rubber, etc. In some embodiments, the recovered olefin such as propylene, isobutene can be sent to an alkylation unit.

In some embodiments, the process recovery unit can also receive a fourth gaseous stream that can be recovered as an overhead product from a primary fractionator that receives and separates various products from a stream cracker effluent produced in a steam cracker. For example, the primary fractionator can separate a steam cracker effluent into a tar product, a steam cracker quench oil product, a steam cracker gas oil product, a steam cracker naphtha product, and a steam cracker gaseous overhead product that can include hydrogen, methane, ethane, ethylene, propane, propylene, butenes, butane, pentane, and other gaseous products.

In some embodiments, the fourth gaseous stream can already be compressed. In other embodiments, the fourth gaseous stream can be combined with the third gaseous stream and the combined gas stream can be compressed to produce a combined third and fourth compressed gaseous stream that can be introduced into the product recovery zone.

In some embodiments, at least a portion of the coked catalyst particles in the recovered entrained coked catalyst particle stream can be conveyed to a metal reclamation facility. In such embodiment, at least a portion of the metal element, e.g., a Group 8-10 element(s), can be recovered from the coked catalyst particles in the recovered entrained catalyst particles stream. In some embodiments, the at least a portion of the coked catalyst particles conveyed to the metal reclamation facility can be done so in the form of a sludge or a cake. In some embodiments, the liquid in the sludge or cake can include a portion of the second quench medium. In other embodiments, the entrained coked catalyst particles can be substantially separated from the second quench medium and conveyed in the form of fluidized particles. In still other embodiments, the entrained coked catalyst particles can be substantially separated from the second quench medium and mixed with another liquid medium to form another slurry, a sludge, or a cake that can be conveyed to the metal reclamation facility. The recovered Group 8-10 element(s) can be reused to make new catalyst particles, purified and sold, for example as a commodity, or used for any other desired purpose.

In some embodiments, the electricity used in the combustion zone can be from renewable sources such as solar, wind, geothermal, hydroelectric, etc. In some embodiments, pure $O_2$ can be used in the combustion zone so that the capture and sequestration of $CO_2$ made during combustion can be facilitated. In some embodiments, the feed can be liquefied petroleum gas which includes of both $C_3$ and $C_4$ paraffinic molecules. In some embodiments, the feed can be one or more components in a natural gas liquid, commonly known as NGL. In some embodiments, the feed can come from a renewable source such as biomass fermentation or transformation.

In some embodiments, at least a portion of the Group 8-10 element(s) can be recovered from the coked catalyst particles via any suitable process or combination of processes. Suitable processes for reclaiming at least a portion of the Group 8-10 element(s) can include, but are not limited to, those described in U.S. Pat. No. 7,033,480; U.S. Patent Application Publication No.: 2004/0219082; Great Britain Patent Application Publication No. GB829972A; Chinese Patent No. CN101760627; and/or Chinese Patent Publication No. CN104831071A.

Dehydrogenation Catalyst Particles

The dehydrogenation catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of Group 8-10 element, e.g., Pt, disposed on a support, based on the weight of the support. In some embodiments, the catalyst particles can include≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 wt % of the Group 8-10 element disposed on the support, based on the weight of the support. In some embodiments, the catalyst particles can include >0.001, >0.003 wt %, >0.005 wt %, >0.007, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of Group 8-10 element disposed on the support, based on the weight of the support. In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt.

In some embodiments, the catalyst particles can optionally include two or more Group 8-10 elements, e.g., Pt and Ni and/or Pd. If two or more Group 8-10 elements are disposed on the support the catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of all Group 8-10 elements disposed on the support, based on the weight of the support. In some embodiments, an active component of the catalyst particles that can be capable of effecting dehydrogenation of a hydrocarbon feed can include the Group 8-10 element(s).

In some embodiments, the catalyst particles can optionally include a promoter in an amount of up to 10 wt % disposed on the support, based on the weight of the support. The promoter, if present, can be or can include, but is not limited to, Sn, Ga, Zn, Ge, In, Re, Ag, Au, Cu, a combination thereof, or a mixture thereof. In at least one embodiment, the promoter can be or can include Sn. In some embodiments, the promoter can be associated with the Group 8-10 element. For example, the promoter and Pt disposed on the support can form Pt-promoter clusters that can be dispersed on the support. The promoter can improve the selectivity/activity/longevity of the catalyst particles for a given upgraded hydrocarbon. In some embodiments, the promoter can improve the propylene selectivity of the catalyst particles when the hydrocarbon-containing feed includes propane. The catalyst particles can include the promoter in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the catalyst particles can optionally include one or more alkali metal elements in an amount of up to 5 wt % disposed on the support, based on the weight of the support. The alkali metal element, if present, can be or can include, but is not limited to, Li, Na, K, Rb, Cs, a combination thereof, or a mixture thereof. In at least one embodiment, the alkali metal element can be or can include K and/or Cs. In at least some embodiments, the alkali metal element ca be or can include K and/or Cs. In some embodiments, the alkali metal element, if present, can improve the selectivity of the catalyst particles for a given upgraded hydrocarbon. The catalyst particles can include the alkali metal element in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

The support can be or can include, but is not limited to, one or more Group 2 elements, a combination thereof, or a mixture thereof. In some embodiments, the Group 2 element can be present in its elemental form. In other embodiments, the Group 2 element can be present in the form of a compound. For example, the Group 2 element can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element can be present in different forms. For example, a first compound can be an oxide and a second compound can be an aluminate where the first compound and the second compound include the same or different Group 2 element, with respect to one another.

The support can include ≥0.5 wt %, ≥1 wt %, ≥2 wt %, ≥3 wt %, ≥4 wt %, ≥5 wt %≥6 wt %, ≥7 wt %, ≥8 wt %, ≥9 wt %, ≥10 wt %, ≥11 wt %, ≥12 wt %, ≥13 wt %, ≥14 wt %, ≥15 wt %, ≥16 wt %, ≥17 wt %, ≥18 wt %, ≥19 wt %, ≥20 wt %, ≥21 wt %, ≥22 wt %, ≥23 wt %, ≥24 wt %, ≥25 wt %, ≥26 wt %, ≥27 wt %, ≥28 wt %, ≥29 wt %, ≥30 wt %, ≥35 wt %, ≥40 wt %, ≥45 wt %, ≥50 wt %, ≥55 wt %, ≥60 wt %, ≥65 wt %, ≥70 wt %, ≥75 wt %, ≥80 wt %, ≥85, or ≥90 wt % of the Group 2 element, based on the weight of the support. In some embodiments, the support can include the Group 2 element in a range from 0.5 wt %, 1 wt %, 2 wt %, 2.5 wt %, 3 wt %, 5 wt %, 7 wt %, 10 wt %, 11 wt %, 13 wt %, 15 wt %, 17 wt %, 19 wt %, 21 wt %, 23 wt %, or 25 wt % to 30 wt %, 35 wt %, 40 wt %, 45 wt %, 50 wt %, 55 wt %, 60 wt %, 65 wt % 70 wt %, 75 wt %, 80 wt %, 85 wt %, 90 wt %, or 92.34 wt % based on the weight of the support. In some embodiments, a molar ratio of the Group 2 element to the Group 8-10 element(s) present can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, or 900,000.

In some embodiments, the support can include the Group 2 element and Al and can be in the form of a mixed Group 2 element/Al metal oxide that has O, Mg, and Al atoms mixed on an atomic scale. In some embodiments, the support can be or can include the Group 2 element and Al in the form of an oxide or one or more oxides of the Group 2 element and $Al_2O_3$ that can be mixed on a nm scale. In some embodiments, the support can be or can include an oxide of the Group 2 element, e.g., MgO, and $Al_2O_3$ mixed on a nm scale.

In some embodiments, the support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support can be or can include, but is not limited to, one or more of the following compounds: $Mg_wAl_2O_3+w$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$; $BaCO_3$; $CaZrO_3$; $Ca_7ZrAl_6O_{18}$; $CaTiO_3$; $Ca_7Al_6O_{18}$; $Ca_7HfAl_6O_{18}$; $BaCeO_3$; one or more magnesium chromates, one or more magnesium tungstates, one or more magnesium molybdates, combinations thereof, and mixtures thereof. In some embodiments, the Group 2 element can include Mg and at least a portion of the Group 2 element can be in the form of MgO or a mixed oxide that includes MgO. In some embodiments, the support can be or can include, but is not limited to, a $MgO—Al_2O_3$ mixed metal oxide. In some embodiments, when the support is a $MgO—Al_2O_3$mixed metal oxide, the support can have a molar ratio of Mg to Al equal to 20, 10, 5, 2, 1 to 0.5, 0.1, or 0.01.

The $Mg_wAl_2O_{3+w}$, where w is a positive number, if present as the support or as a component of the support can have a molar ratio of Mg to Al in a range from 0.5, 1, 2, 3, 4, or 5 to 6, 7, 8, 9, or 10. In some embodiments, the $Mg_wAl_2O_{3+w}$ can include $MgAl_2O_4$, $Mg_2Al_2O_5$, or a mixture thereof. The $Ca_xAl_2O_{3+x}$, where x is a positive number, if present as the support or as a component of the support can have a molar ratio of Ca to Al in a range from 1:12, 1:4, 1:2, 2:3, 5:6, 1:1, 12:14, or 1.5:1. In some embodiments, the $Ca_xAl_2O_{3+x}$ can include tricalcium aluminate, dodecacalcium hepta-aluminate, monocalcium aluminate, monocalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support can have a molar ratio of Ba to Al 0.05, 0.3, or 0.6 to 0.9, 1.5, or 3.

In some embodiments, the support can also include, but is not limited to, at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga. If the support also includes a compound that includes the metal element and/or metalloid element selected from Groups other than Group 2 and Group 10, where the at least one metal element and/or at least one metalloid element is not Li, Na, K, Rb, Cs, Sn, Cu, Au, Ag, or Ga, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga can be or can include, but is not limited to, one or more rare earth elements, i.e., elements having an atomic number of 21, 39, or 57 to 71.

If the support includes the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element can, in some embodiments, function as a binder and can be referred to as a "binder". Regardless of whether or not the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element selected from Groups other than Group 2 and Group 10 will be further described herein as a "binder" for clarity and ease of description. It is known that in literature, some of the compounds herein referred to as "binders" may also be referred to as fillers, matrix, an additive, etc. In some embodiments, the support can include the binder in a range from 0.01 wt %, 0.05 wt %, 0.1 wt %, 0.5 wt %, 1 wt %, 5 wt %, 10 wt %, 15 wt %, 20 wt %, 25 wt %, 30 wt %, 35 wt % or 40 wt % to 50 wt %, 60 wt %, 70 wt %, 80 wt %, or 90 wt % based on the weight of the support.

In some embodiments, suitable compounds that include the binder can be or can include, but are not limited to, one or more of the following: $B_2O_3$, $AlBO_3$, $Al_2O_3$, $SiO_2$, $ZrO_2$, $TiO_2$, SiC, $Si_3N_4$, an aluminosilicate, zinc aluminate, ZnO, VO, $V_2O_3$, $VO_2$, $V_2O_5$, $Ga_sO_t$, $In_uO_v$, $Mn_2O_3$, $Mn_3O_4$, MnO, one or more molybdenum oxides, one or more tungsten oxides, one or more zeolites, where s, t, u, and v are positive numbers and mixtures and combinations thereof.

The catalyst particles can have a median particle size in a range from 1 μm, 5 μm, 10 μm, 20 μm, 40 μm, or 60 μm to 80 μm, 100 μm, 115 μm, 130 μm, 150 μm, 200 μm, 300 μm or 400, or 500 μm. The catalyst particles can have an apparent loose bulk density in a range from 0.3 $g/cm^3$, 0.4 $g/cm^3$, 0.5 $g/cm^3$, 0.6 $g/cm^3$, 0.7 $g/cm^3$, 0.8 $g/cm^3$, 0.9 $g/cm^3$, or 1 g/cm3 to 1.1 $g/cm^3$, 1.2 $g/cm^3$, 1.3 $g/cm^3$, 1.4 $g/cm^3$, 1.5 $g/cm^3$, 1.6 $g/cm^3$, 1.7 $g/cm^3$, 1.8 $g/cm^3$, 1.9 $g/cm^3$, or 2 $g/cm^3$, as measured according to ASTM D7481-18 modified with a 10, 25, or 50 ml graduated cylinder instead of a 100 or 250 mL graduated cylinder. In some embodiments, the catalyst particles can have an attrition loss after one hour of <5 wt %, <4 wt %, <3 wt %, <2 wt %, ≤1 wt %, ≤0.7 wt %, ≤0.5 wt %, ≤0.4 wt %, ≤0.3 wt %, ≤0.2 wt %, ≤0.1 wt %, ≤0.07 wt %, or ≤0.05 wt %, as measured according to ASTM D5757-11 (2017). The morphology of the particles is largely spherical so that they are suitable to run in a fluid bed reactor. In some embodiments, the catalyst particles can have a size and density that is consistent with a Geldart A or Geldart B definition of a fluidizable solid.

In some embodiments, the catalyst particles can have a surface area in a range from 0.1 $m^2/g$, 1 $m^2/g$, 10 $m^2/g$, or 100 $m^2/g$ to 500 $m^2/g$, 800 $m^2/g$, 1,000 $m^2/g$, or 1,500 $m^2/g$. The surface area of the catalyst particles can be measured according to the Brunauer-Emmett-Teller (BET) method using adsorption-desorption of nitrogen (temperature of liquid nitrogen, 77 K) with a Micromeritics 3flex instrument after degassing of the powders for 4 hrs at 350° C. More information regarding the method can be found, for example, in "Characterization of Porous Solids and Powders: Surface Area, Pore Size and Density," S. Lowell et al., Springer, 2004.

The preparation of the support can be accomplished via any known process. For simplicity and ease of description, the preparation of a suitable support that includes a mixed oxide of magnesium and aluminum (Mg(Al) O or MgO/$Al_2O_3$) support will be described in more detail. Catalyst synthesis techniques are well-known and the following description is for illustrative purposes and not to be considered as limiting the synthesis of the support or the catalyst particles. In some embodiments, to make the MgO/$Al_2O_3$mixed oxide support, Mg and Al precursors such as $Mg(NO_3)_2$ and $Al(NO_3)_3$ can be mixed together, e.g., ball-milled, followed by calcination to produce the support. In another embodiment, the two precursors can be dissolved in $H_2O$, stirred until dry (with heat optionally applied), followed by calcination to produce the support. In another embodiment, the two precursors can be dissolved in $H_2O$, followed by the addition of a base and a carbonate, e.g., $NaOH/Na_2CO_3$ to produce hydrotalcite, followed by calcination to produce the support. In another embodiment, a commercial ready MgO and $Al_2O_3$ may be mixed and ball-milled. In another embodiment, the $Mg(NO_3)_2$ precursor can be dissolved in $H_2O$ and the solution can be impregnated onto an existing support, e.g., an $Al_2O_3$ support, that can be dried and calcined to produce the support. In another embodiment, Mg from $Mg(NO_3)$ 2 can be loaded onto an existing $Al_2O_3$ support through ion adsorption, followed by liquid-solid separation, drying and calcination to produce the support. Without wishing to be bound by theory, it is believed that the support produced via any one of the above methods and/or other methods can include (i) the Mg and Al mixed together on the nm scale, (ii) the Mg and Al in the form of a mixed Mg/Al metal oxide, or (iii) a combination of (i) and (ii).

Group 8-10 metals and any promoter and/or any alkali metal element may be loaded onto the mixed oxide support by any known technique. For example, one or more Group 8-10 element precursors, e.g., chloroplatinic acid, tetramineplatinum nitrate, and/or tetramineplatinum hydroxide, one or more promoter precursors (if used), e.g., a salt such as $SnCl_4$ and/or $AgNO_3$, and one or more alkali metal element precursors (if used), e.g., $KNO_3$, KCl, and/or NaCl, can be dissolved in water. The solution can be impregnated onto the support, followed by drying and calcination. In some embodiments, the Group 8-10 element precursor and optionally the promoter precursor and/or the alkali metal element precursor can be loaded onto the support at the same time, or separately in a sequence separated by drying and/or calcination steps. In other embodiments, the Group 8-10 element and, optionally the promoter and/or alkali metal element, can be loaded onto the support by chemical vapor deposition, where the precursors are volatilized and deposited onto the support, followed by calcination. In other embodiments, the Group 8-10 element precursor and, optionally, the promoter precursor and/or alkali metal precursor, can be loaded onto the support through ion adsorption, followed by liquid-solid separation, drying and calcination. Optionally, the catalyst particles can also be synthesized using a one-pot synthesis method where the precursors of the support, group 8-10 metal active phase and the promoters are all mixed together, dry or wet, with or without any other additives to aid the synthesis, followed by drying and calcination.

In some embodiments, the catalyst particles can be formulated into Geldart A or B type particles via the well-known spray drying process. Spray-dried catalyst particles having an average cross-sectional area in a range from 20 μm, 40 μm, or 50 μm to 80 μm, 90 μm, or 100 μm are typically used in an FCC type fluid-bed reactor. To make spray-dried catalyst particles, the support, the Group 8-10 element, and any additional components, e.g., the promoter and/or the alkali metal, can be made into a slurry with binder/additive in the slurry before spray-drying and calcination. Alternatively, the Group 8-10 element, and any additional components, e.g., the promoter and/or the alkali metal, can be added to the formulated support to produce the formulated catalyst particles.

Suitable processes that can be used to prepare the catalyst particles disclosed herein can include the processes described in U.S. Pat. Nos. 4,788,371; 4,962,265; 5,922,925; 8,653,317; EP Patent No. EP0098622; Journal of Catalysis 94 (1985), pp. 547-557; and/or Applied Catalysis 54 (1989), pp. 79-90.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst particles. In some embodiments, the hydrocarbon in the hydrocarbon-containing feed can be composed of substantially a single alkane such as propane. In some embodiments, the hydrocarbon-containing feed can include $\geq 50$ mol %, $\geq 75$ mol %, $\geq 95$ mol %, $\geq 98$ mol %, or $\geq 99$ mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatic hydrocarbons can be or can include, but are not limited to, ethylbenzene, propylbenzene, butylbenzene, one or more ethyl toluenes, or a mixture thereof. In some embodiments, the hydrocarbon-containing feed can include $\geq 50$ mol %, $\geq 75$ mol %, $\geq 95$ mol %, $\geq 98$ mol %, or $\geq 99$ mol % of a single $C_5$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyl toluene dehydrogenation, and the like.

In some embodiments, the hydrocarbon-containing feed can be diluted with one or more diluent gases. Suitable diluents can be or can include, but are not limited to, argon, neon, helium, molecular nitrogen, carbon dioxide, methane, molecular hydrogen, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatic hydrocarbons in the hydrocarbon-containing feed. When the diluent includes molecular hydrogen, a molar ratio of the molecular hydrogen to a combined amount of any $C_2$-$C_{16}$ alkane and any $C_8$-$C_{16}$ alkyl aromatic hydrocarbons can be in a range from 0.1, 0.3, 0.5, 0.7, or 1 to 2, 3, 4, 5, 6, 7, 8, 9, or 10. In some embodiments, if the diluent is used, the diluent can be mixed with the hydrocarbon-containing feed and/or introduced or otherwise fed into the conversion zone as a separate feed via one or more inlets dedicated to feeding the diluent into the conversion zone. Similarly, the hydrocarbon-containing feed can also be introduced into the conversion zone via one or more inlets dedicated to feeding the hydrocarbon-containing feed into the conversion zone.

In some embodiments, the hydrocarbon-containing feed can be substantially free of any water or steam, e.g., <0.1 vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include $\leq 50$ vol %, $\leq 45$ vol %, $\leq 40$ vol %, $\leq 35$ vol %, $\leq 30$ vol %, $\leq 25$ vol %, $\leq 20$ vol %, or $\leq 15$ vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of water or steam, based on a total volume of any $C_2$-$C_{16}$ alkanes and any $C_8$-$C_{16}$ alkyl aromatic hydrocarbons in the hydrocarbon-containing feed. Similar to the diluent, if water or steam is fed into the conversion zone, the water or steam can be fed into the conversion zone as a component of the hydrocarbon-containing feed or via one or more separate inlets dedicated to introducing the steam into the conversion zone.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof. In some embodiments, the sulfur can be introduced into the conversion zone as a separate feed, as a component of the diluent if used, and/or as a component of the steam if used.

The hydrocarbon-containing feed can be substantially free or free of molecular oxygen. In some embodiments, the hydrocarbon-containing feed can include $\leq 5$ mol %, $\leq 3$ mol %, or $\leq 1$ mol % of molecular oxygen ($O_2$). It is believed that providing a hydrocarbon-containing feed substantially-free of molecular oxygen substantially prevents oxidative coupling reactions that would otherwise consume at least a portion of the alkane and/or the alkyl aromatic hydrocarbon in the hydrocarbon-containing feed.

Exemplary Embodiments

FIG. 1 depicts a system 100 for dehydrogenating a hydrocarbon-containing feed in line 1001, according to one or more embodiments. The system 100 can include a reactor or conversion zone 1010, a separation zone 1015, a direct quench zone 1020, a combustion zone 1025, a reduction zone 1035, a quench zone 1040, a compression zone 1050, and a product recovery zone 1055. In some embodiments, the system 100 can optionally include a hydrocarbon-containing feed pretreatment zone 1005. In some embodiments, the system 100 can optionally include an oxygen soak zone 1030. The hydrocarbon-containing feed via line 1001 or a pre-treated hydrocarbon-containing feed via line 1007 can be introduced into the conversion zone 1010, e.g., at a bottom end of a fluidized bed reactor such as a riser reactor or an upper end of a downer reactor. In some embodiments, the hydrocarbon-containing feed in line 1001 and/or the pre-treated hydrocarbon-containing feed in line 1007 can include steam. Regenerated catalyst particles via line 1036 can be conveyed from the reduction zone 1035 to the conversion zone 1010. The hydrocarbon-containing feed can be contacted with the regenerated catalyst particles in the conversion zone 1010 to effect dehydrogenation of at least a portion of the hydrocarbon-containing feed to produce a conversion effluent via line 1013 that can include coked catalyst particles, one or more dehydrogenated hydrocarbons, unreacted hydrocarbon-containing feed, steam, benzene, or any mixture thereof.

The conversion effluent via line 1013 can be introduced into the separation zone 1015 that can separate the conversion effluent into a first particle stream via 1017 rich in the coked catalyst particles and a first gaseous stream via line 1019 rich in the one or more dehydrogenated hydrocarbons and including entrained coked catalyst particles. In some embodiments, the separation zone can include one or more cyclones arranged in series and/or arranged in parallel.

The first particle stream via line 1017 can be introduced into the combustion zone 1025. In some embodiments, the first particle stream can include entrained gaseous components such as the one or more dehydrogenated hydrocarbons, unreacted hydrocarbon-containing feed, steam, or a mixture thereof. In such embodiment, at least a portion of the gaseous components in the first particle stream in line 1017 can be stripped off before the first particle stream is introduced into the combustion zone 1025. An oxidant via line 1022 and optionally a fuel via line 1024 can be introduced into the combustion zone 1025 that can contact at least a portion of the coked catalyst particles in the first particle stream to effect combustion of at least a portion of the coke, and, if present, the fuel to produce a combustion effluent that includes catalyst particles lean in coke and a combustion or flue gas. The combustion of the coke and, if present fuel, can produce heat to burn the coke from the coked catalyst, re-disperse the Group 8-10 element(s) on the spent catalyst and add heat to the regenerated catalyst particles.

A second particle stream rich in the catalyst particles lean in coke via line 1026 and a second gaseous stream rich in the combustion gas via line 1027 can be recovered or otherwise obtained from the combustion zone 1025. The combustion effluent can enter into one or more separation devices to return a majority of the entrained catalysts back to the combustion zone. For the combustion zone, sometimes three or more stages of cyclones can be installed to achieve a higher solid recovery efficiency from the flue gas. The residual catalyst particles can be further recovered downstream by using a filter, an electrostatic precipitator, a wet gas scrubber, etc. The separation devices and/or the operating conditions of cyclones on the conversion and combustion zone can be tuned to deliver a higher or lower amount of fines from either the conversion zone or the combustion zone, depending on the fine collection difficulty levels from the product stream from the conversion zone versus the flue gas stream from the combustion zone.

When the fuel via line 1024 is introduced into the combustion zone the second particle stream via line 1026 and an oxidative gas via line 1028 can be introduced into the oxygen soak zone 1030 and contacted therein to produce conditioned catalyst particles. The conditioned catalyst particles via line 1031 and a gaseous stream via line 1032 can be recovered from the oxygen soak zone 1030. In some embodiments, the gaseous stream in line 1032 and the conditioned catalyst particles in line 1031 can be separated via one or more cyclones. In some embodiments, the same set of cyclones can be used to separate both the conditioned catalyst particles via line 1031 and the gaseous stream via line 1032 and the second particle stream via line 1026 and the combustion gas via line 1027.

The conditioned catalyst particles via line 1031 or when the fuel is not introduced via line 1024 into the combustion zone the second particle stream via line 1026 and a reducing gas via line 1033 can be introduced into the reduction zone 1035 and contacted therein to produce regenerated catalyst particles. The regenerated catalyst particles via line 1036 and a gaseous stream via line 1037 can be recovered from the reduction zone. In some embodiments, the regenerated catalyst particles in line 1036 and the gaseous stream in line 1037 can be separated via one or more cyclones. In other embodiments, the gaseous components within the reduction zone can be conveyed to the conversion zone 1010 with the regenerated catalyst particles via line 1036 rather than being separated therefrom. The regenerated catalyst particles via line 1036 can be introduced into the conversion zone 1010 and contacted with additional hydrocarbon-containing feed therein. In some embodiments, the gaseous stream in line 1037 can be recycled to the combustion zone so that any residual reducing as such as $H_2$ can serve as a fuel for the combustion zone.

The first gaseous stream via line 1019 and a first quench medium via line 1018 can be introduced into the direct quench zone 1020 and contacted therein to produce a cooled gaseous stream. In some embodiments, benzene can be produced during the dehydrogenation of the hydrocarbon-containing feed and can be present in the cooled gaseous stream in line 1021. In some embodiments, benzene can be used as the first quench medium in line 1018. In some embodiments, the first quench medium stream can be in the liquid phase when contacted with the first gaseous stream in the direct quench zone 1020. In some embodiments, first gaseous stream in line 1019 can be at a temperature >620° C. and the cooled gaseous stream can be at a temperature of ≤620° C., ≤610° C., ≤600° C., ≤590° C., or ≤580° C. In some embodiments, the cooled gaseous stream can be at a temperature in a range of ≥550° C. and ≤620° C. or ≤600° C. Reducing the temperature of the first gaseous stream in line 1019 to less than 600° C. can reduce or stop undesirable thermal reactions of the gas components. The cooled gaseous stream can be recovered via line 1021. In some embodiments, the direct quench zone 1020 can be replaced with one or more indirect heat exchange zones. In other embodiments, one or more indirect heat exchange zones can be used in conjunction with the direct quench zone 1020 either upstream and/or downstream of the direct quench zone 1020.

The cooled gaseous stream via line 1021 and a second quench medium via line 1022 can be introduced into the quench zone 1040 and contacted therein to produce an overhead or third gaseous stream via line 1041, a recovered fine-lean second quench medium via line 1042, and a recovered coked catalyst particles stream via line 1043. In some embodiments, the quench zone 1040 can include a quench tower. In some embodiments, the cooled gaseous stream via line 1021 can be introduced into a gas-liquid contact zone disposed within the quench tower. In some embodiments, as noted above, before entering the contacting zone, the cooled gaseous stream via line 1021 can also pass through one or more heat exchangers for heat recovery. In the contact zone disposed within the quench tower, the cooled gaseous stream can contact the second quench medium introduced via line 1022 into the quench tower. The second quench medium in line 1022 can be sprayed downward into the contact zone counter-current to the cooled gaseous stream to ensure good contact between the cooled gaseous stream and the second quench medium. In the contact zone a majority of the catalyst fines and heat in the cooled gaseous stream can be transferred to the second quench medium to produce a slurry that can include at least a portion of the second quench medium in the liquid phase and at least a portion of the coked catalyst particles. In some embodiments, the slurry can accumulate at the bottom of the quench tower to form a liquid reservoir therein. In some embodiments, the second quench medium in line 1022 can have a normal boiling point greater than the first quench medium 1018. For example, in some embodiments, the first quench medium can be benzene and the second quench medium can have a normal boiling point of 150° C. to 580° C.

In the quench zone 1040 the slurry can be introduced into one or more solid-liquid separation devices to produce the recovered fines-lean second quench medium stream via line 1042 and the recovered coked catalyst particles stream via line 1043. In some embodiments, at least a portion of the recovered coked catalyst particles stream via line 1043 can be introduced into the optional metal reclamation facility 1060. In one or more embodiments, at least a portion of the recovered coked catalyst particles stream via line 1043 can be introduced into the combustion zone 1025. In one or more embodiments, at least a portion of the recovered fines-lean second quench medium via line 1042 can be recycled back to the quench tower within the quench zone 1040.

In some embodiments, at the locations above the gas-liquid contact zone in the quench tower, the first quench medium, with a normal boiling point less than the second quench medium, can be withdrawn from the quench tower, cooled via one or more heat exchangers, and a first portion or quantity can be circulated back into the direct contact zone via line 1018. In some embodiments, a second portion or quantity of the cooled first quench medium can be withdrawn to form a product stream, since the first quench medium can be one of the products of alkane dehydrogenation, benzene. In some embodiments, a third portion or quantity of the cooled first quench medium can be recycled to the quench tower.

At the locations above the contact zone within the quench tower, any water present in the quench tower can be withdrawn from the quench tower, cooled down through one or more heat exchangers, and circulated back into the quench tower. A portion or quantity of the cooled water can be withdrawn to form a wastewater stream that can be sent for treatment and/or vaporized and used as a co-feed with the hydrocarbon-containing stream in line 1001 or the pretreated hydrocarbon containing feed in line 1007.

The third gaseous stream via line 1041 coming out of the quench zone 1040 can be essentially free of coked catalyst particles and it can then be further cooled introduced into the compression zone 1050 to produce a compressed gaseous stream via line 1051. If the third gaseous stream in line 1041 contains any remaining coked catalyst particles, such coked catalyst particles can be removed via one or more electrostatic precipitators, one or more filters, one or more screens, one or more membranes, wet gas scrubber, contact with an absorbent scavenger, one or more additional quench towers, one or more electrocyclones, one or more hydrocyclones, one or more centrifuges, one or plates or cones, or any combination thereof to remove at least a portion of the entrained coked catalyst particles therefrom.

The compressed gaseous stream via line 1051 can be introduced into the product recovery zone 1055 to separate products therefrom. In some embodiments, the products can include, but are not limited to, light gases via line 1056, unreacted hydrocarbon-containing feed via line 1057, one or more dehydrogenated hydrocarbons via line 1058, and one or more liquid hydrocarbons via line 1059. The one or more light gases can be or can include, but are not limited to, hydrogen, methane, ethane, propane, butane, or any mixture thereof. In some embodiments, the one or more of the light gases via line 1056 can be introduced into the combustion zone via line 1024 as the optional fuel. In some embodiments, at least a portion of the unreacted hydrocarbon-containing feed can be recycled via line 1057 to the conversion zone. In some embodiments, the dehydrogenated hydrocarbons in line 1058 can be further processed to produce one or more products such as polyethylene, polypropylene, and/or other polymer products. In some embodiments, at least a portion of the one or more liquid hydrocarbons in line 1059 can be used as the first and/or second quench mediums or used as a quench medium elsewhere.

In some embodiments, a fourth gaseous stream via line 1053 can also be introduced into the product recovery zone 1055. The fourth gaseous stream in line 1053 can be in fluid communication with a primary fractionator that receives a steam cracker effluent and separates various hydrocarbon fractions therefrom. For example, the primary fractionator can separate a steam cracker effluent into a tar product, a steam cracker quench oil product, a steam cracker gas oil product, a steam cracker naphtha product, and a steam cracker gaseous overhead product that can include hydrogen, methane, ethane, ethylene, propane, propylene, butenes, butane, pentane, and other volatile hydrocarbons. In some embodiments, the fourth gaseous stream in line 1053 can be compressed. In other embodiments, the fourth gaseous stream in via line 1053 can be combined with the third gaseous stream in line 1041 and introduced into the compression zone 1050 to produce a combined third and fourth compressed gaseous stream in line 1051.

EXAMPLES

The foregoing discussion can be further described with reference to the following non-limiting examples.

Catalyst Composition 1: was prepared by mixing CATAPAL® D pseudoboehmite (Sasol) (47 g) and calcined Mg—Al hydrotalcite (PURALOX® MG70) (44 g) that contained 70 wt % MgO and 30 wt % $Al_2O_3$ in deionized water (524 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % $Al_2O_3$ derived from CATAPAL® D. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 50:50 MG70: CATAPAL® D.

Catalyst Composition 2: was prepared by mixing 40 wt % aluminum chlorohydrol solution (ACH) (85 g) and calcined Mg—Al hydrotalcite (PURALOX® MG70) (88 g) in deionized water (596 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 80 wt % PURALOX® MG70 and 20 wt % $Al_2O_3$ derived from ACH. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 80:20 MG70: ACH.

Catalyst Composition 3: The catalyst was prepared according to the following procedure: Set aside 2.3 g PURALOX® MG 70/170 (Sasol), which was a MgO—$Al_2O_3$ mixed metal oxide that was obtained by calcining hydrotalcite. The mixed metal oxide contained 70 wt % MgO and 30 wt % $Al_2O_3$. The BET surface area was 170 $m^2/g$ according to Sasol. Tin (IV) chloride pentahydrate (0.103 g) (Acros Organics), chloroplatinic acid hexahydrate (0.0184 g) (BioXtra), and deionized water (2.2 mL) were mixed in a small glass vial to make a solution. The PURALOX® MG 70/170 support was impregnated with the solution. The impregnated material was dried at 110° C. for 6 hours, and calcined at 800° C. for 12 hours, all in air. The final product contained nominally 0.3 wt % Pt and 1.5 wt % Sn.

Catalyst Composition 4: The catalyst was prepared according to the following procedure: Set aside 20 g PURALOX® MG 70/170 (Sasol), which was a MgO—$Al_2O_3$ mixed metal oxide obtained by calcining hydrotalcite. The mixed metal oxide contained 70 wt % MgO and 30 wt % $Al_2O_3$. The BET surface area was 170 $m^2/g$ according to Sasol. An appropriate amount of tin (II) chloride dehydrate and deionized water were mixed to form a solution. The PURALOX® MG 70/170 support was impregnated with the solution. The impregnated material was stored in a closed container at room temperature for 1 h before it was dried at 120° C. overnight. An appropriate amount of tetraammineplatinum (II) nitrate and deionized water were mixed to form a solution. The support impregnated with Sn was further impregnated with the Pt solution. The impregnated material was sitting in a closed container at room temperature for 1 h before it was dried at 120° C. overnight and calcined at 800° C. for 12 hours, all in air. The final product contained nominally 0.3 wt % Pt and 1.5 wt % Sn.

Catalyst Compositions 5-18 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 $m^2/g$, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours. Table 1 shows the nominal Pt and Sn content of each catalyst composition based on the weight of the support.

TABLE 1

| Catalyst | Pt (wt %) | Sn (wt %) |
|---|---|---|
| 5 | 0.4 | 1 |
| 6 | 0.3 | 1 |
| 7 | 0.2 | 1 |
| 8 | 0.1 | 1 |
| 9 | 0.05 | 1 |
| 10 | 0.025 | 1 |
| 11 | 0.0125 | 1 |
| 12 | 0 | 1 |
| 13 | 0.1 | 0.5 |
| 14 | 0.1 | 1 |
| 15 | 0.1 | 2 |
| 16 | 0.0125 | 0 |
| 17 | 0.0125 | 0.5 |
| 18 | 0.0125 | 2 |

Examples Using Catalysts 1-4 Described Above

Fixed bed experiments were conducted at ~100 kPa-absolute. A gas chromatograph (GC) was used to measure the composition of the reactor effluents. The concentration of each component in the reactor effluents were then used to calculate the $C_3H_6$ yield and selectivity. The $C_3H_6$ yield and selectivity, as reported in these examples, were calculated on the carbon mole basis.

In each example, 0.3 g of catalyst Mcat was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The concentration of each component in the reactor effluent was used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the tables below.

Figure 2:
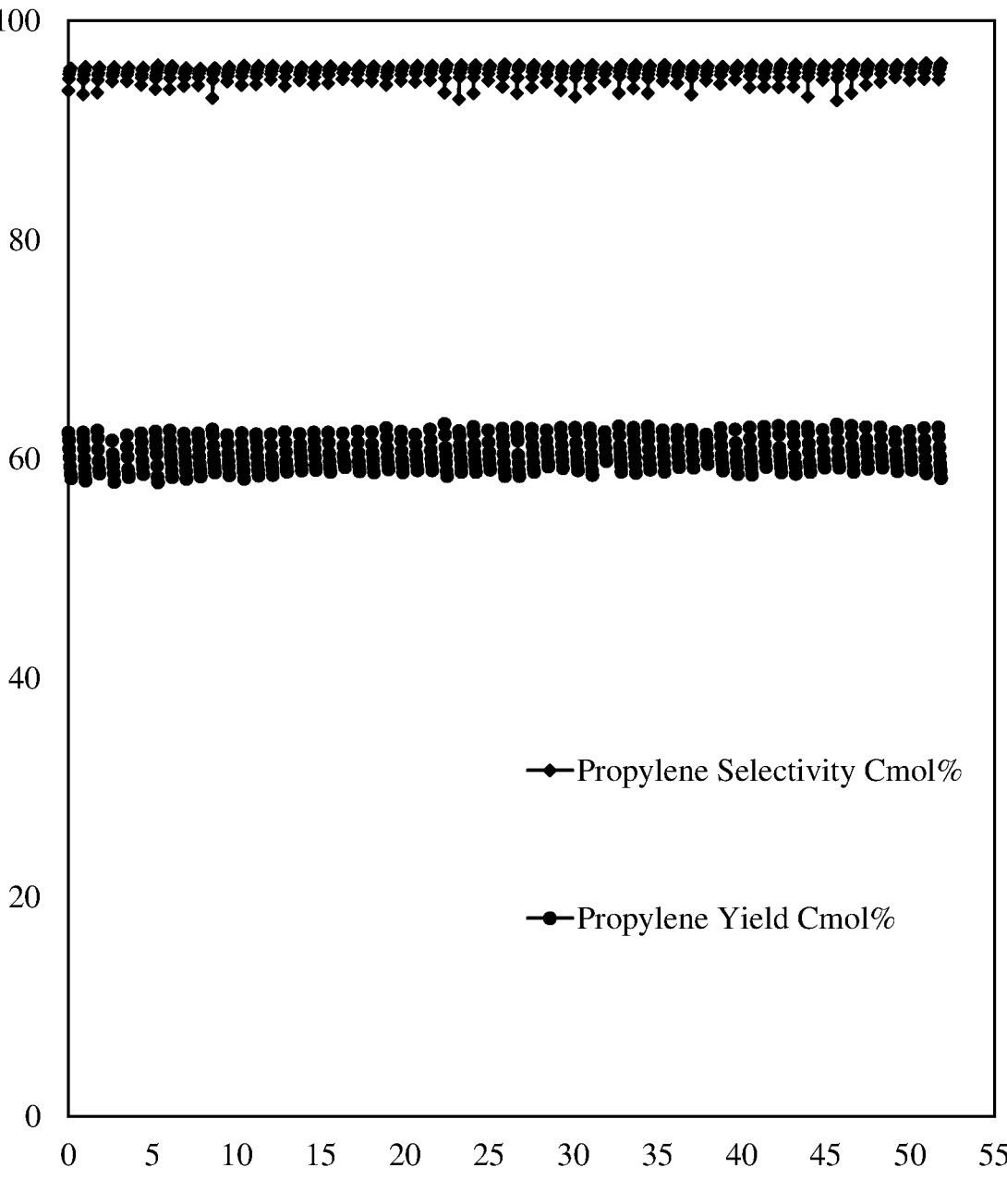
FIG. 2 shows a catalyst composition was stable for over 60 cycles for propane dehydrogenation.

The process steps for Examples 1 and 2 were as follows: 1. The system was flushed with an inert gas. 2. An oxygen containing gas (Ogas) at a flow rate ($F_{regen}$) was passed through the by-pass of the reaction zone, while an inert was passed through the reaction zone. The reaction zone was heated to a regeneration temperature $T_{regen}$. 3. The oxygen containing gas was then passed through the reaction zone for a certain period of time ($t_{regen}$) to regenerate the catalyst. After $t_{regen}$, the temperature within the reaction zone was changed from $T_{regen}$ to a reduction temperature ($T_{red}$) while maintaining the oxygen-containing gas flow. 4. The system was flushed with an inert gas. 5. A $H_2$ containing gas (Hgas) at a flow rate ($F_{red}$) was passed through the by-pass of the reaction zone for a certain period of time, while an inert was passed through the reaction zone. This is then followed by flowing the $H_2$ containing gas through the reaction zone at $T_{red}$ for a certain period of time ($t_{red}$). 6. The system was flushed with an inert. During this process, the temperature of the reaction zone was changed from $T_{red}$ to a reaction temperature of 655° C. 7. A hydrocarbon-containing (HC-gas) feed that included 81 vol % $C_3H_8$, 9 vol % inert (Ar or Kr) and 10 vol % steam at a flow rate ($F_{rxn}$) was passed through the by-pass of the reaction zone for a certain period of time, while an inert was passed through the reaction zone. The hydrocarbon-containing feed was then passed through the reaction zone at 655° C. for 10 min. GC sampling of the reaction effluent started as soon as the feed was switched from the by-pass of the reaction zone to the reaction zone. The above process steps were repeated in cycles until stable performance was obtained. Table 2 shows that both catalyst 1 and 2 were active/selective for propane dehydrogenation. FIG. 2 shows that catalyst 2 was stable over 60 cycles for propane dehydrogenation.

TABLE 2

| Catalyst | 1 | 2 |
|---|---|---|
| $M_{cat}$ (g) | 0.3 | 0 |
| $F_{rxn}$ (sccm) | 17.6 | 17.6 |
| Hgas | 10% $H_2$, 90% Ar | 10% $H_2$, 90% Ar |
| $F_{red}$ (sccm) | 46.6 | 46.6 |
| $T_{red}$ (° C.) | 800 | 800 |
| $t_{red}$ (min) | 0.05 | 0.05 |
| Ogas | 90% Air, 10% $H_2O$; Then Dry air | 90% Air, 10% $H_2O$; Then Dry air |
| $F_{regen}$ (sccm) | 93.2; Then 83.9 | 93.2; Then 83.9 |
| $T_{regen}$ (° C.) | 800 | 800 |
| $t_{regen}$ (min) | 1; Then 10 | 1; Then 10 |
| Performance  $Y_{ini}$ | 59.4 | 62.9 |
|  $Y_{end}$ | 52.4 | 59.2 |
|  $S_{ini}$ | 95.3 | 94.4 |
|  $S_{end}$ | 96.3 | 95.9 |

Example 3-Effect of steam during oxidation. The process steps were as follows: 1. The system was flushed with an inert gas while the reaction zone was heated to an oxidation temperature $T_{oxi}$. 2. An oxygen containing gas (Ogas) at a flow rate ($F_{oxi}$) was passed through the by-pass of the reaction zone, while an inert was passed through the reaction zone. 3. The oxygen containing gas was then passed through the reaction zone for a certain period of time ($t_{oxi}$) to oxidize the catalyst. 4. After $t_{oxi}$, an inert was passed through the reaction zone and the temperature within the reaction zone was changed from $T_{oxi}$ to a reduction temperature ($T_{red}$). 5. The system was flushed with an inert gas. 6. A $H_2$ containing gas (Hgas) at a flow rate ($F_{red}$) was passed through the by-pass of the reaction zone for a certain period of time, while an inert was passed through the reaction zone. This was then followed by flowing the $H_2$ containing gas through the reaction zone at $T_{red}$ for a certain period of time ($t_{red}$). 7. The system was flushed with an inert. During this process, the temperature of the reaction zone was changed from $T_{red}$ to a reaction temperature of 670° C. 8. A hydrocarbon-containing (HCgas) feed that included 81 vol % $C_3H_8$, 9 vol % inert (Ar or Kr) and 10 vol % steam at a flow rate ($F_{rxn}$) was passed through the by-pass of the reaction zone for a certain period of time, while an inert was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone. The above process steps were repeated in cycles until stable performance was obtained. Table 3 shows that the presence of more than 10 vol % of steam in air during oxidation yielded an even more deactivated catalyst after regeneration ($C_3H_6$ yield of 56.8% vs 61.1%). The more steam present in air during oxidation, the lower the activity. On the other hand, if the moist air was switched to dry air after 2 min of oxidation, the catalyst was effectively regenerated.

TABLE 3

| Catalyst | 3 | 3 | 3 | 3 |
|---|---|---|---|---|
| $M_{cat}$ (g) | 0.3 | 0.3 | 0.3 | 0.3 |
| $F_{rxn}$ (sccm) | 17.6 | 17.6 | 17.6 | 17.6 |
| Hgas | 10% $H_2$ 90% Ar | 10% $H_2$ 90% Ar | 10% $H_2$ 90% Ar | 10% $H_2$ 90% Ar |
| $F_{red}$ (sccm) | 46.6 | 46.6 | 46.6 | 46.6 |

TABLE 3-continued

| Catalyst | 3 | 3 | 3 | 3 |
|---|---|---|---|---|
| $T_{red}$ (° C.) | 750 | 750 | 750 | 750 |
| $t_{red}$ (min) | 0.05 | 0.05 | 0.05 | 0.05 |
| Ogas | Dry air | 95.7% Air 4.3% $H_2O$ | 90% Air 10% $H_2O$ | 90% Air 10% $H_2O$ Then Dry air |
| $F_{oxi}$ (sccm) | 46.6 | 48.7 | 51.7 | 51.7; Then 46.6 |
| $T_{oxi}$ (° C.) | 800 | 800 | 800 | 800 |
| $t_{oxi}$ (min) | 10 | 10 | 10 | 2; Then 8 |
| Performance  $Y_{ini}$ | 65.1 | 61.2 | 56.8 | 63.7 |
|  $Y_{end}$ | 61.1 | 56.5 | 51.3 | 58.6 |
|  $S_{ini}$ | 95.2 | 95.5 | 95.2 | 95.1 |
|  $S_{end}$ | 95.9 | 96.0 | 95.4 | 95.9 |

Example 4—Effect of $H_2$ reduction duration. 1. The system was flushed with an inert gas while the reaction zone was heated to an oxidation temperature of 800° C. 2. An oxygen containing gas (Ogas) at a flow rate ($F_{oxi}$) was passed through the by-pass of the reaction zone, while an inert was passed through the reaction zone. 3. The oxygen containing gas was then passed through the reaction zone for a certain period of time ($t_{oxi}$) to oxidize the catalyst. 4. The system was flushed with an inert gas. During this process, the temperature of the reaction zone was kept at 800° C. 5. A $H_2$ containing gas (Hgas) at a flow rate ($F_{red}$) was passed through the by-pass of the reaction zone for a certain period of time, while an inert was passed through the reaction zone. This was then followed by flowing the $H_2$ containing gas through the reaction zone at 800° C. for a certain period of time ($t_{red}$). 6. The reaction zone was passed with He. During this process, the temperature of the reaction zone was reduced from 800° C. to a reaction temperature of 655° C. 7. A hydrocarbon-containing (HCgas) feed that included 81 vol % $C_3H_8$, 9 vol % inert (Ar or Kr) and 10 vol % steam at a flow rate (Fran) was passed through the by-pass of the reaction zone for a certain period of time, while an inert was passed through the reaction zone. The hydrocarbon-containing feed was then passed through the reaction zone at 655° C. for 10 min. GC sampling of the reaction effluent started as soon as the feed was switched from the by-pass of the reaction zone to the reaction zone. The above process steps were repeated in cycles until stable performance was obtained. Table 4 shows that without catalyst reduction, the propylene yield of the oxidized catalyst (53.7%) was even lower than that of the deactivated catalyst (61.3%).

TABLE 4

| Catalyst | 4 | 4 |
|---|---|---|
| $M_{cat}$ (g) | 0.3 | 0.3 |
| $F_{rxn}$ (sccm) | 17.6 | 17.6 |
| Hgas | 10% $H_2$; 90% Ar | 10% $H_2$; 90% Ar |
| $F_{red}$ (sccm) | 46.6 | 46.6 |
| $t_{red}$ (min) | 0 | 0.05 |
| Ogas | 90% Air 10% $H_2O$; Then Dry air | 90% Air 10% $H_2O$; Then Dry air |
| $F_{oxi}$ (sccm) | 93.2; Then 83.9 | 93.2; Then 83.9 |
| $t_{oxi}$ (min) | 1; Then 10 | 1; Then 10 |
| Performance  $Y_{ini}$ | 53.7 | 63.3 |
|  $Y_{end}$ | 37.9 | 61.3 |
|  $S_{ini}$ | 93.1 | 94.5 |
|  $S_{end}$ | 95.9 | 96.1 |

Example 5-Fixed bed experiments were conducted at approximately 100 kPa-absolute that used catalysts 5-18. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in Tables 5 and 6 below for catalyst compositions 5-12.

The process steps for catalyst compositions 5-12 were as follows: 1. The system was flushed with an inert gas. 2. Dry air at a flow rate of 83.9 sccm was passed through a by-pass of the reaction zone, while an inert was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_3$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone. The above process steps were repeated in cycles until stable performance was obtained. Tables 5 and 6 show that catalyst composition 10 that contained only 0.025 wt % of Pt and 1 wt % of Sn had both a similar yield and a similar selectivity as compared to catalyst composition 5 that contained 0.4 wt % of Pt and 1 wt % of Sn, which was surprising and unexpected. Catalyst composition 12 that did not include any Pt did not show an appreciable propylene yield.

TABLE 5

| | | Catalyst 5 | Catalyst 6 | Catalyst 7 | Catalyst 8 |
|---|---|---|---|---|---|
| Performance | $Y_{ini}$ | 61.7 | 61.7 | 60.7 | 63.7 |
| | $Y_{end}$ | 55.2 | 55.7 | 54.2 | 56.7 |
| | $S_{ini}$ | 97.3 | 97.2 | 97.0 | 97.1 |
| | $S_{end}$ | 98.1 | 98.0 | 97.7 | 98.3 |

TABLE 6

| | | Catalyst 9 | Catalyst 10 | Catalyst 11 | Catalyst 12 |
|---|---|---|---|---|---|
| Performance | $Y_{ini}$ | 62.4 | 62.0 | 56.7 | 2.0 |
| | $Y_{end}$ | 57.2 | 54.6 | 45.7 | 1.7 |

TABLE 6-continued

| | | Catalyst 9 | Catalyst 10 | Catalyst 11 | Catalyst 12 |
|---|---|---|---|---|---|
| | $S_{ini}$ | 96.7 | 97.3 | 96.9 | 64.2 |
| | $S_{end}$ | 97.7 | 98.0 | 97.6 | 49.5 |

Catalyst compositions 13-18 were also tested using the same process steps 1-7 described above with regard to catalysts 5-12. Table 7 shows that the level of Sn should not be too low or too high for optimal propylene yield for the catalyst compositions that included 0.1 wt % of Pt based on the weight of the support.

TABLE 7

| | | Catalyst 13 0.5 wt % Sn | Catalyst 8 1 wt % Sn | Catalyst 14 1 wt % Sn | Catalyst 15 2 wt % Sn |
|---|---|---|---|---|---|
| Performance | $Y_{ini}$ | 58.4 | 63.7 | 63.4 | 56.5 |
| | $Y_{end}$ | 49.5 | 56.7 | 55.5 | 47.7 |
| | $S_{ini}$ | 96.9 | 97.1 | 97.2 | 97.8 |
| | $S_{end}$ | 97.6 | 98.3 | 98.1 | 98.2 |

Table 8 shows that the level of Sn should not be too high or too low for optimal propylene yield for the catalyst compositions that included 0.0125 wt % of Pt based on the weight of the support.

TABLE 8

| | | Catalyst 16 0 wt % Sn | Catalyst 17 0.5 wt % Sn | Catalyst 11 1 wt % Sn | Catalyst 18 2 wt % Sn |
|---|---|---|---|---|---|
| Performance | $Y_{ini}$ | 2.6 | 44 | 56.7 | 55.4 |
| | $Y_{end}$ | 1.7 | 24.4 | 45.7 | 44.1 |
| | $S_{ini}$ | 63.9 | 96.7 | 96.9 | 96.8 |
| | $S_{end}$ | 61.1 | 95.6 | 97.6 | 97.6 |

Figure 3:
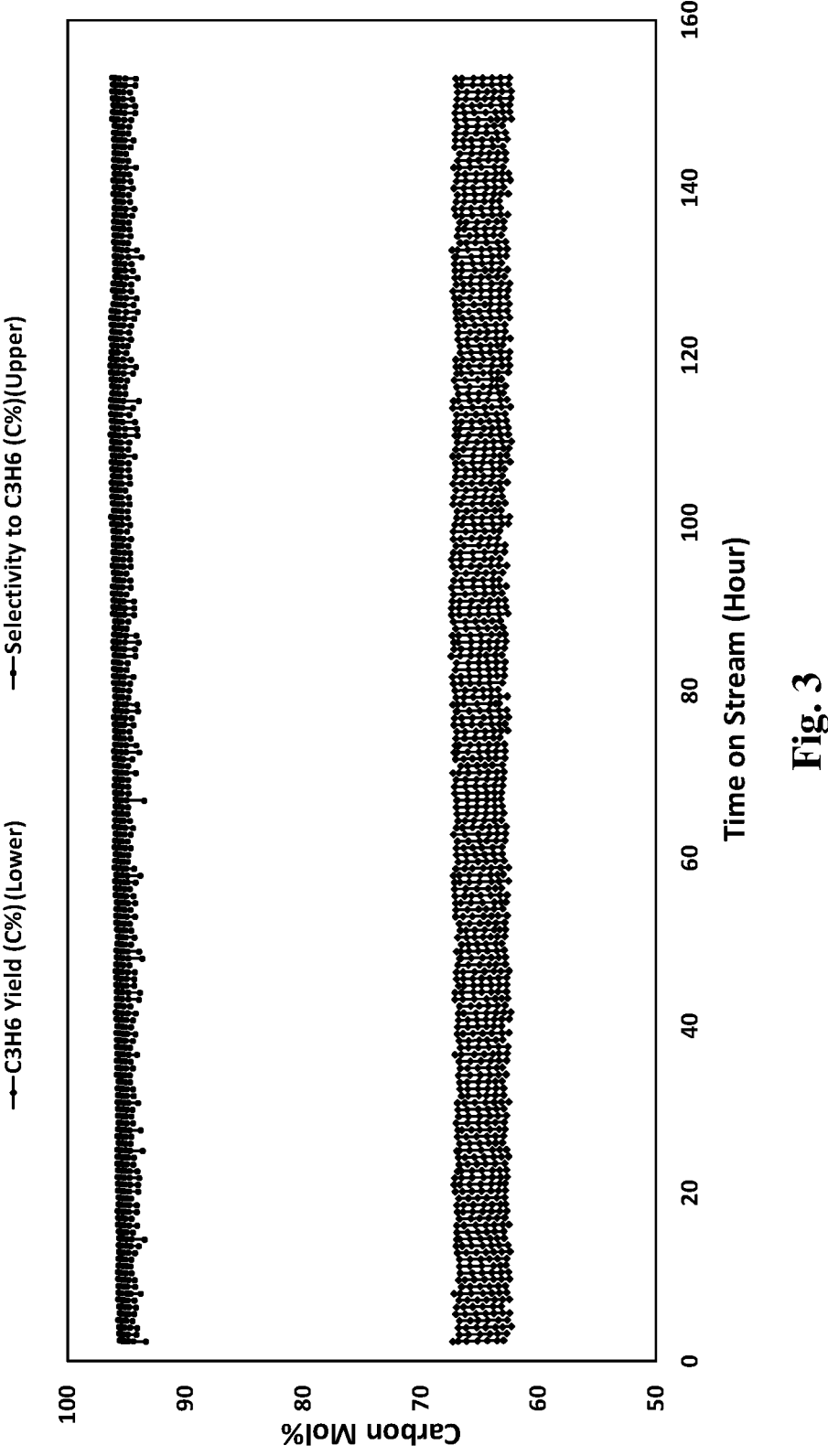
FIG. 3 shows a catalyst composition (catalyst 10) maintained its performance for 204 cycles.

Catalyst composition 10 that contained only 0.025 wt % of Pt and 1 wt % of Sn was also subjected to a longevity test using the same process steps 1-7 described above with regard to catalyst compositions 5-12, except a flow rate of 17.6 sccm was used instead of 35.2 sccm in step 7. FIG. 3 shows that catalyst composition 10 maintained performance for 204 cycles (x-axis is time, y-axis is $C_3H_6$ yield and selectivity to $C_3H_6$, both in carbon mole %).

Listing of Embodiments

This disclosure may further include the following non-limiting embodiments.

A1. A process for upgrading a hydrocarbon, comprising: (I) contacting a hydrocarbon-containing feed with fluidized dehydrogenation catalyst particles in a conversion zone to effect dehydrogenation of at least a portion of the hydrocarbon-containing feed to produce a conversion effluent comprising coked catalyst particles and one or more dehydrogenated hydrocarbons, wherein: the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof, the hydrocarbon-containing feed contacts the catalyst particles at a weight hourly space velocity in a range from 0.1 $hr^{-1}$ to 1,000 $hr^{-1}$, based on the weight of any $C_2$-$C_{16}$ alkanes and any $C_5$-$C_{16}$ aromatic hydrocarbons in the hydrocarbon-containing feed, a weight ratio of the fluidized dehydrogenation catalyst particles to a combined amount of any $C_2$-$C_{16}$ alkanes and any $C_5$-$C_{16}$ aromatic hydrocarbons is in a range from 3 to 100, and the hydrocarbon-containing feed and the catalyst particles are contacted at a temperature in a range from 600° C. to 750° C.; (II) separating from the conversion effluent a first particle stream rich in the coked catalyst particles and a first gaseous stream rich in the one or more dehydrogenated hydrocarbons; (III) contacting at least a portion of the coked catalyst particles in the first particle stream with an oxidant in a combustion zone to effect combustion of at least a portion of the coke to produce a combustion effluent comprising catalyst particles lean in coke and a combustion gas, wherein a dehydrogenation activity of the catalyst particles lean in coke is less than a dehydrogenation activity of the coked catalyst particles, and wherein the combustion zone is heated via an electrical heater; (IV) separating a second particle stream rich in the catalyst particles lean in coke and a second gaseous stream rich in the combustion gas from the combustion effluent; (V) contacting at least a portion of the second particle stream with a reducing gas in a reduction zone to produce regenerated catalyst particles having a dehydrogenation activity that is greater than the coked catalyst particles; (VI) contacting an additional quantity of the hydrocarbon-containing feed with at least a portion of the regenerated catalyst particles in the conversion zone to produce an additional quantity of the conversion effluent comprising re-coked catalyst particles and an additional quantity of the one or more dehydrogenated hydrocarbons; (VII) cooling the first gaseous stream to produce a cooled gaseous stream; (VIII) compressing at least a portion of the cooled gaseous stream to produce a compressed gaseous stream; and (IX) separating a plurality of products from the compressed gaseous stream.

A2. The process of A1, wherein no supplemental hydrocarbon fuel is introduced into the combustion zone.

A3. The process of A1 or A2, wherein any hydrocarbon present within the combustion zone comprises entrained hydrocarbons from the conversion effluent.

A4. The process of any one of A1 to A3, wherein the hydrocarbon-containing feed contacts the fluidized dehydrogenation catalyst particles at a weight hourly space velocity in a range from 0.1 hr$^{-1}$ to 100 hr$^{-1}$, preferably from 0.2 hr$^{-1}$ to 64 hr$^{-1}$, or more preferably from 0.4 hr$^{-1}$ to 32 hr$^{-1}$, based on the weight of any $C_2$-$C_{16}$ alkanes and any $C_8$-$C_{16}$ aromatic hydrocarbons in the hydrocarbon-containing feed.

A5. The process of any one of A1 to A4, wherein a weight ratio of the fluidized dehydrogenation catalyst particles to a combined amount of any $C_2$-$C_{16}$ alkanes and any $C_8$-$C_{16}$ aromatic hydrocarbons is in a range from 5 to 90, or more preferably from 10 to 80.

A6. The process of any one of A1 to A5, wherein the hydrocarbon-containing feed is contacted with the fluidized dehydrogenation catalyst particles for a duration of 0.1 seconds to 2 minutes, preferably 1 second to 1 minute, more preferably 0.5 seconds to 3 seconds.

A7. The process of any one of A1 to A6, wherein the hydrocarbon-containing feed is contacted with the fluidized dehydrogenation catalyst particles under a total pressure in a range from 0 kPa-gauge to 500 kPa-gauge, preferably from 20 kPa-gauge to 300 kPa-gauge, or more preferably from 40 kPa-gauge to 200 kPa-gauge.

A8. The process of any one A1 to A7, wherein the hydrocarbon-containing feed comprises 0.1 mol % to 15 mol % of steam, preferably 1 mol % to 10 mol % of steam, or more preferably 3 mol % to 8 mol % of steam.

A9. The process of any one of A1 to A8, wherein the hydrocarbon-containing feed is at temperature of ≤620° C. when initially contacted with the fluidized dehydrogenation catalyst particles.

A10. The process of any one of A1 to A9, wherein the second particle stream is contacted with the reducing gas in step (V) at a temperature in a range from 450° C. to 900° C., preferably from 600° C. to 900° C., more preferably from 620° C. to 800° C.

A11. The process of any one of A1 to A10, wherein the second particle stream is contacted with the reducing gas in step (V) for a duration of 0.1 second to 300 seconds, preferably from 1 second to 100 seconds, more preferably from 2 seconds to 10 seconds to produce the regenerated catalyst particles.

A12. The process of any one of A1 to A11, wherein: the first gaseous stream rich in the one or more dehydrogenated hydrocarbons further comprises entrained coked catalyst particles, step (VII) comprises: (VIIa) contacting the first gaseous stream with a first quench medium, indirectly transferring heat from the first gaseous stream to a first heat transfer medium, or a combination thereof, to produce the cooled gaseous stream, and (VIIb) contacting the cooled gaseous stream with a second quench medium within a quench tower, (VIIc) recovering a third gaseous stream comprising the one or more dehydrogenated hydrocarbons and a slurry stream comprising at least a portion of the second quench medium in a liquid phase and the entrained coked catalyst particles from the quench tower, and step (VIII) comprises compressing at least a portion of the third gaseous stream to produce the compressed gaseous stream.

A13. The process of A12, wherein the conversion effluent further comprises benzene, the process further comprising (X) withdrawing a benzene product stream from the quench tower.

A14. The process of A12 or A13, wherein step (VIIa) comprises contacting the first gaseous stream with the first quench medium.

A15. The process of any one of A1 to A11, wherein the first particle stream and the first gaseous stream are separated from the conversion effluent within one or more cyclones, and wherein the first gaseous stream is contacted with a first quench medium within at least one plenum of the one or more cyclones in step (VII) to produce the cooled gaseous stream.

A16. The process of A15, wherein a residence time of the gaseous components in the first gaseous steam within each of the one or more cyclones is ≤1 second.

A17. The process of any one of A1 to A16, wherein the conversion effluent is at a temperature of ≥620° C. and the cooled gaseous stream is at a temperature of ≥500° C. and <620° C., preferably ≥550° C. to ≤600° C.

A18. The process of any one of A1 to A17, wherein the dehydrogenation catalyst particles comprise 0.001 wt % to 6 wt % of a Group 8-10 element and optionally up to 10 wt % of a promoter comprising Sn, Cu, Au, Ag, Ga, a combination thereof, or a mixture thereof disposed on a support, and wherein all weight percent values are based on the weight of the support.

A19. The process of any one of A1 to A18, wherein the dehydrogenation catalyst particles comprise 0.001 wt % to 6 wt % of Pt and optionally up to 10 wt % of a promoter comprising Sn, Cu, Au, Ag, Ga, a combination thereof, or a mixture thereof disposed on a support, wherein the support comprises at least 0.5 wt % of a Group 2 element, and wherein all weight percent values are based on the weight of the support.

A20. The process of any one of A1 to A19, wherein dehydrogenation catalyst particles meet the requirements of a Geldart A or Geldart B classification.

A21. The process of any one of A1 to A20, wherein the plurality of products is separated from the compressed gaseous stream in step (IX) in a product recovery unit that also receives a gaseous overhead product separated from a primary fractionator that receives a pyrolysis effluent from a stream cracker furnace.

A22. The process of any one of A1 to A21, wherein the hydrocarbon-containing feed comprises propane derived from biomass.

A23. The process of any one of A1 to A22, wherein the hydrocarbon-containing feed comprises liquefied petroleum gas.

A24. The process of any one of A1 to A23, wherein the oxidant used in step (III) comprises ≥95 mol % of $O_2$.

A25. The process of any one of A1 to A24, wherein the conversion zone and the combustion zone are located within a retrofitted fluidized catalytic cracking reactor-regenerator unit.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:
(I) contacting a hydrocarbon-containing feed with fluidized dehydrogenation catalyst particles in a conversion zone to effect dehydrogenation of at least a portion of the hydrocarbon-containing feed to produce a conversion effluent comprising coked catalyst particles and one or more dehydrogenated hydrocarbons, wherein:
the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof,
the hydrocarbon-containing feed contacts the catalyst particles at a weight hourly space velocity in a range from 0.1 $hr^{-1}$ to 1,000 $hr^{-1}$, based on the weight of any $C_2$-$C_{16}$ alkanes and any $C_8$-$C_{16}$ aromatic hydrocarbons in the hydrocarbon-containing feed,
a weight ratio of the fluidized dehydrogenation catalyst particles to a combined amount of any $C_2$-$C_{16}$ alkanes and any $C_8$-$C_{16}$ aromatic hydrocarbons is in a range from 3 to 100, and
the hydrocarbon-containing feed and the catalyst particles are contacted at a temperature in a range from 600° C. to 750° C.;
(II) separating from the conversion effluent a first particle stream rich in the coked catalyst particles and a first gaseous stream rich in the one or more dehydrogenated hydrocarbons;
(III) contacting at least a portion of the coked catalyst particles in the first particle stream with an oxidant and a fuel in a combustion zone to effect combustion of at least a portion of the coke to produce a combustion effluent comprising catalyst particles lean in coke and a combustion gas, wherein a dehydrogenation activity of the catalyst particles lean in coke is less than a dehydrogenation activity of the coked catalyst particles;
(IV) separating a second particle stream rich in the catalyst particles lean in coke and a second gaseous stream rich in the combustion gas from the combustion effluent;
(V) contacting at least a portion of the catalyst particles lean in coke in the second particle stream with an oxidative gas in an oxygen soak zone at an oxidizing temperature in a range from 620° C. to 1,000° C. for a duration of at least 20 seconds to produce conditioned catalyst particles having an activity that is less than the coked catalyst particles, wherein the oxidative gas comprises no greater than 5% $H_2O$ based on the total moles in the oxidative gas;
(VI) contacting at least a portion of the conditioned catalyst particles with a reducing gas in a reduction zone to produce regenerated catalyst particles having a dehydrogenation activity that is greater than the coked catalyst particles;
(VII) contacting an additional quantity of the hydrocarbon-containing feed with at least a portion of the regenerated catalyst particles in the conversion zone to produce an additional quantity of the conversion effluent comprising re-coked catalyst particles and an additional quantity of the one or more dehydrogenated hydrocarbons;
(VIII) cooling the first gaseous stream to produce a cooled gaseous stream;
(IX) compressing at least a portion of the cooled gaseous stream to produce a compressed gaseous stream; and
(X) separating a plurality of products from the compressed gaseous stream.

2. The process of claim 1, wherein the hydrocarbon-containing feed contacts the fluidized dehydrogenation catalyst particles at a weight hourly space velocity in a range from 0.1 $hr^{-1}$ to 100 $hr^{-1}$, based on the weight of any $C_2$-$C_{16}$ alkanes and any $C_8$-$C_{16}$ aromatic hydrocarbons in the hydrocarbon-containing feed.

3. The process of claim 1, wherein a weight ratio of the fluidized dehydrogenation catalyst particles to a combined amount of any $C_2$-$C_{16}$ alkanes and any $C_8$-$C_{16}$ aromatic hydrocarbons is in a range from 5 to 90.

4. The process of claim 1, wherein the hydrocarbon-containing feed is contacted with the fluidized dehydrogenation catalyst particles for a duration of 0.1 seconds to 2 minutes.

5. The process of claim 1, wherein the hydrocarbon-containing feed is contacted with the fluidized dehydrogenation catalyst particles under a total pressure in a range from 0 kPa-gauge to 500 kPa-gauge.

6. The process of claim 1, wherein the hydrocarbon-containing feed comprises 0.1 mol % to 15 mol % of steam.

7. The process of claim 1, wherein the hydrocarbon-containing feed is at temperature of ≤620° C. when initially contacted with the fluidized dehydrogenation catalyst particles.

8. The process of claim 1, wherein the catalyst particles lean in coke in the second particle stream are contacted with the oxidative gas in step (V) for a duration of 0.5 minutes to 30 minutes.

9. The process of claim 1, wherein the conditioned catalyst particles are contacted with the reducing gas in step (VI) at a temperature in a range from 450° C. to 900° C.

10. The process of claim 1, wherein the conditioned catalyst particles are contacted with the reducing gas in step (VI) for a duration of 0.1 second to 300 seconds to produce the regenerated catalyst particles.

11. The process of claim 1, wherein:

the first gaseous stream rich in the one or more dehydrogenated hydrocarbons further comprises entrained coked catalyst particles, step (VIII) comprises:

(VIIIa) contacting the first gaseous stream with a first quench medium, indirectly transferring heat from the first gaseous stream to a first heat transfer medium, or a combination thereof, to produce the cooled gaseous stream, and (VIIIb) contacting the cooled gaseous stream with a second quench medium within a quench tower, (VIIIc) recovering a third gaseous stream comprising the one or more dehydrogenated hydrocarbons and a slurry stream comprising at least a portion of the second quench medium in a liquid phase and the entrained coked catalyst particles from the quench tower, and step (IX) comprises compressing at least a portion of the third gaseous stream to produce the compressed gaseous stream.

12. The process of claim 11, wherein the conversion effluent further comprises benzene, the process further comprising (XI) withdrawing a benzene product stream from the quench tower.

13. The process of claim 11, wherein step (VIIIa) comprises contacting the first gaseous stream with the first quench medium.

14. The process of claim 1, wherein the first particle stream and the first gaseous stream are separated from the conversion effluent within one or more cyclones, and wherein the first gaseous stream is contacted with a first quench medium within at least one plenum of the one or more cyclones in step (VIII) to produce the cooled gaseous stream.

15. The process of claim 14, wherein a residence time of the gaseous components in the first gaseous steam within each of the one or more cyclones is ≤1 second.

16. The process of claim 1, wherein the conversion effluent is at a temperature of ≥620° C. and the cooled gaseous stream is at a temperature of ≥500° C. and <620° C.

17. The process of claim 1, wherein the dehydrogenation catalyst particles comprise 0.001 wt % to 6 wt % of a Group 8-10 element and optionally up to 10 wt % of a promoter comprising Sn, Cu, Au, Ag, Ga, a combination thereof, or a mixture thereof disposed on a support, and wherein all weight percent values are based on the weight of the support.

18. The process of claim 1, wherein the dehydrogenation catalyst particles comprise 0.001 wt % to 6 wt % of Pt and optionally up to 10 wt % of a promoter comprising Sn, Cu, Au, Ag, Ga, a combination thereof, or a mixture thereof disposed on a support, wherein the support comprises at least 0.5 wt % of a Group 2 element, and wherein all weight percent values are based on the weight of the support.

19. The process of claim 1, wherein dehydrogenation catalyst particles meet the requirements of a Geldart A or Geldart B classification.

20. The process of claim 1, wherein the plurality of products is separated from the compressed gaseous stream in step (X) in a product recovery unit that also receives a gaseous overhead product separated from a primary fractionator that receives a pyrolysis effluent from a stream cracker furnace.

21. The process of claim 1, wherein the hydrocarbon-containing feed comprises propane derived from biomass.

22. The process of claim 1, wherein the hydrocarbon-containing feed comprises liquefied petroleum gas.

23. The process of claim 1, wherein the oxidant used in step (III) comprises ≥95 mol % of $O_2$.

24. The process of claim 1, wherein the conversion zone and the combustion zone are located within a retrofitted fluidized catalytic cracking reactor-regenerator unit.

25. The process of claim 1, wherein the dehydrogenated catalyst particles comprise a support comprising Al in the form of an oxide and a Group 2 element.

* * * * *